US010546049B2

(12) United States Patent
Grady et al.

(10) Patent No.: US 10,546,049 B2
(45) Date of Patent: *Jan. 28, 2020

(54) SYSTEMS AND METHODS FOR VALIDATING AND CORRECTING AUTOMATED MEDICAL IMAGE ANNOTATIONS

(71) Applicant: HeartFlow, Inc., Redwood City, CA (US)

(72) Inventors: Leo J. Grady, Millbrae, CA (US); Romain Moreau-Gobard, Redwood City, CA (US); Michiel Schaap, Mountain View, CA (US)

(73) Assignee: HeartFlow, Inc., Redwood City, CA (US)

(*) Notice: Subject to any disclaimer, the term of this patent is extended or adjusted under 35 U.S.C. 154(b) by 32 days.

This patent is subject to a terminal disclaimer.

(21) Appl. No.: 14/971,095

(22) Filed: Dec. 16, 2015

(65) Prior Publication Data

US 2016/0103816 A1   Apr. 14, 2016

Related U.S. Application Data

(63) Continuation of application No. 14/495,789, filed on Sep. 24, 2014, now Pat. No. 9,304,982.

(Continued)

(51) Int. Cl.
*G06F 17/00* (2019.01)
*G06F 17/24* (2006.01)
(Continued)

(52) U.S. Cl.
CPC ............ *G06F 17/241* (2013.01); *A61B 6/032* (2013.01); *A61B 6/468* (2013.01);
(Continued)

(58) Field of Classification Search
CPC ..... G06F 17/241; G06K 9/00456; G06K 9/48
(Continued)

(56) References Cited

U.S. PATENT DOCUMENTS 7,783,074 B2 * 8/2010 Shi ................... G06T 1/0028
382/100
8,315,812 B2 11/2012 Taylor
(Continued)

FOREIGN PATENT DOCUMENTS

WO    WO 01/11548 A1    2/2001
WO       2006128302 A1   12/2006
WO    WO 2008/020062 A1  2/2008

OTHER PUBLICATIONS

Charles A. Taylor et al.: "*Computational Fluid Dynamics Applied to Cardiac Computed Tomography for Noninvasive Quantification of Fractional Flow Reserve*", Journal of the American College of Cardiology, vol. 61, No. 22, (2013).
(Continued)

*Primary Examiner* — Stephen S Hong
*Assistant Examiner* — Matthew J Ludwig
(74) *Attorney, Agent, or Firm* — Bookoff McAndrews, PLLC

(57) ABSTRACT

Systems and methods are disclosed for manipulating image annotations. One method includes receiving an image of an individual's anatomy; automatically determining, using a processor, one or more annotations for anatomical features identified in the image of the individual's anatomy; determining a dependency or hierarchy between at least two of the one or more annotations for anatomical features identified in the image of the individual's anatomy; and generating, based on the dependency or hierarchy, a workflow (Continued)

prompting a user to manipulate the one or more annotations for anatomical features identified in the image of the individual's anatomy.

15 Claims, 23 Drawing Sheets

Related U.S. Application Data

(60) Provisional application No. 61/882,492, filed on Sep. 25, 2013.

(51) Int. Cl.

| | |
|---|---|
| *G06T 7/00* | (2017.01) |
| *G06F 3/0484* | (2013.01) |
| *G06T 19/00* | (2011.01) |
| *G06F 19/00* | (2018.01) |
| *A61B 6/03* | (2006.01) |
| *A61B 6/00* | (2006.01) |
| *G06T 17/00* | (2006.01) |
| *G06K 9/00* | (2006.01) |
| *G16H 30/20* | (2018.01) |

(52) U.S. Cl.
CPC ........ *G06F 3/04845* (2013.01); *G06F 19/321* (2013.01); *G06K 9/00369* (2013.01); *G06T 7/0012* (2013.01); *G06T 17/00* (2013.01); *G06T 19/00* (2013.01); *G06T 19/003* (2013.01); *G16H 30/20* (2018.01); *G06T 2207/30048* (2013.01); *G06T 2207/30101* (2013.01); *G06T 2207/30196* (2013.01); *G06T 2219/004* (2013.01)

(58) Field of Classification Search
USPC ........ 715/230, 231; 382/140, 176, 190, 128
See application file for complete search history.

(56) References Cited

U.S. PATENT DOCUMENTS

| | | | |
|---|---|---|---|
| 8,600,771 B2 | 12/2013 | Mahesh et al. | |
| 8,654,139 B2 | 2/2014 | Jakobovits | |
| 2007/0253611 A1* | 11/2007 | Rousson | G06K 9/34 |
| | | | 382/128 |
| 2008/0084415 A1 | 4/2008 | Gundel | |
| 2008/0140722 A1* | 6/2008 | Jakobovits | G06F 19/321 |
| 2009/0132285 A1* | 5/2009 | Jakobovits | G06F 3/0482 |
| | | | 705/3 |
| 2009/0274384 A1 | 11/2009 | Jakobovits | |
| 2011/0110568 A1* | 5/2011 | Vesper | G06F 19/321 |
| | | | 382/128 |
| 2012/0172700 A1 | 7/2012 | Krishnan et al. | |

OTHER PUBLICATIONS

Hortense A. Kirisli et al.: "*Fully Automatic Cardiac Segmentation from 3D CTA data: a multi-atlas Based Approach*", Medical Imaging 2010, Proceeding of SPIE. vol. 7623, 762305-9, (2010).

Zheng, et al.: "*Efficient Detection of Native and bypass Coronary Ostia in Cardiac CT Volumes: Anatomical vs. Pathological Structures*," Proc. Int'l Conf. Medical Image computing and Computer Assisted Intervention (2011).

Zhen, Barbu et al.: "*Four-Chamber Heart Modeling and Automatic Segmentation for 3D Cardiac CT Volumes Using Marginal Space Learning and Steerable Features*", IEEE Transactions on Medical Imaging, vol. 27, No. 11, pp. 1668-1681, 2008.

Y. Kitamura et al.: "*Automatic Coronary Extraction by Supervised Detection and Shape Matching*", International Symposium on Biomedical Imaging (ISBI), 2012 9th Institute of Electrical and Electronics Engineers (IEEE) International Symposium on May 2-5, 2012.

C. Lorenz, et al.: "A Comprehensive Shape Model of the Heart", Medical Image Analysis, vol. 10, No. 4, pp. 657-670, May 18, 2006.

M. Schaap et al.: "*Robust Shape Regression for Supervised Vessel Segmentation and its Application to Coronary Segmentation in CTA*" IEEE Transactions on Medical Imaging, vol. 30, No. 11, Nov. 2011.

International Search Report, dated Feb. 6, 2015, for International Appln. No. PCT/US2014/057310, filed Sep. 24, 2014.

European Office Action dated May 22, 2017 in corresponding European Patent Application No. 14 787 314.5.

\* cited by examiner

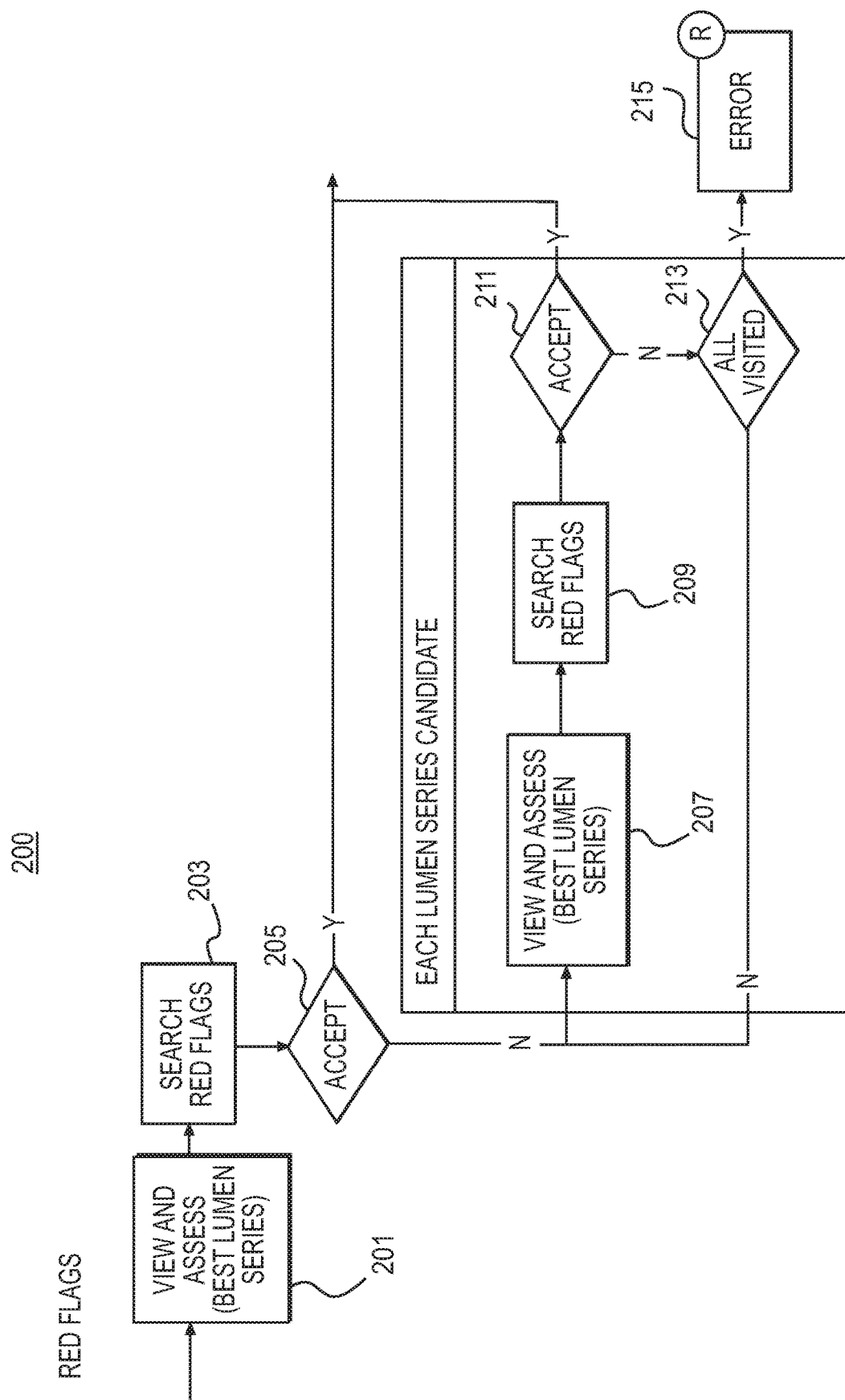

FIG. 3B

SYSTEMS AND METHODS FOR VALIDATING AND CORRECTING AUTOMATED MEDICAL IMAGE ANNOTATIONS

CROSS-REFERENCE TO RELATED APPLICATION(S)

This application is a continuation of U.S. Nonprovisional patent application Ser. No. 14/495,789, filed Sep. 24, 2014, which claims priority to U.S. Provisional Patent Application No. 61/882,492 filed Sep. 25, 2013, the entireties of each of which are incorporated herein by reference.

FIELD OF THE DISCLOSURE

Various embodiments of the present disclosure relate generally to creating accurate models for computational analysis. More specifically, particular embodiments of the present disclosure relate to systems and methods for manipulating or validating and correcting automated image annotations.

BACKGROUND

Automated image annotation plays an increasing role in commercial systems. In particular, the medical imaging community relies increasingly on the automated analysis and annotation of large images. Since this automated image analysis may be used to drive patient care decisions, it is important for the automated results be validated and appropriately corrected (if necessary) by a knowledgeable user. Thus, a desire exists to guide a user through approval or correction of the automated image analysis and annotations.

SUMMARY

According to certain aspects of the present disclosure, systems and methods are disclosed for manipulating image annotations. One method includes: Systems and methods are disclosed for manipulating image annotations. One method includes receiving an image of an individual's anatomy; automatically determining, using a processor, one or more annotations for anatomical features identified in the image of the individual's anatomy; determining a dependency or hierarchy between at least two of the one or more annotations for anatomical features identified in the image of the individual's anatomy; and generating, based on the dependency or hierarchy, a workflow prompting a user to manipulate the one or more annotations for anatomical features identified in the image of the individual's anatomy.

In accordance with another embodiment, a system for manipulating image annotations comprises: a data storage device storing instructions manipulating image annotations; and a processor configured for: receiving an image of an individual's anatomy; automatically determining, using a processor, one or more annotations for anatomical features identified in the image of the individual's anatomy; determining a dependency or hierarchy between at least two of the one or more annotations for anatomical features identified in the image of the individual's anatomy; and generating, based on the dependency or hierarchy, a workflow prompting a user to manipulate the one or more annotations for anatomical features identified in the image of the individual's anatomy.

In accordance with yet another embodiment, a non-transitory computer readable medium for use on a computer system containing computer-executable programming instructions manipulating image annotations is provided. The method includes: receiving an image of an individual's anatomy; automatically determining, using a processor, one or more annotations for anatomical features identified in the image of the individual's anatomy; determining a dependency or hierarchy between at least two of the one or more annotations for anatomical features identified in the image of the individual's anatomy; and generating, based on the dependency or hierarchy, a workflow prompting a user to manipulate the one or more annotations for anatomical features identified in the image of the individual's anatomy.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

FIG. 2 is a block diagram of an exemplary red flags task, according to an exemplary embodiment of the present disclosure.

FIG. 3B is a display of an aorta inspect mode, according to an exemplary embodiment of the present disclosure.

DESCRIPTION OF THE EMBODIMENTS

Figure 1A:
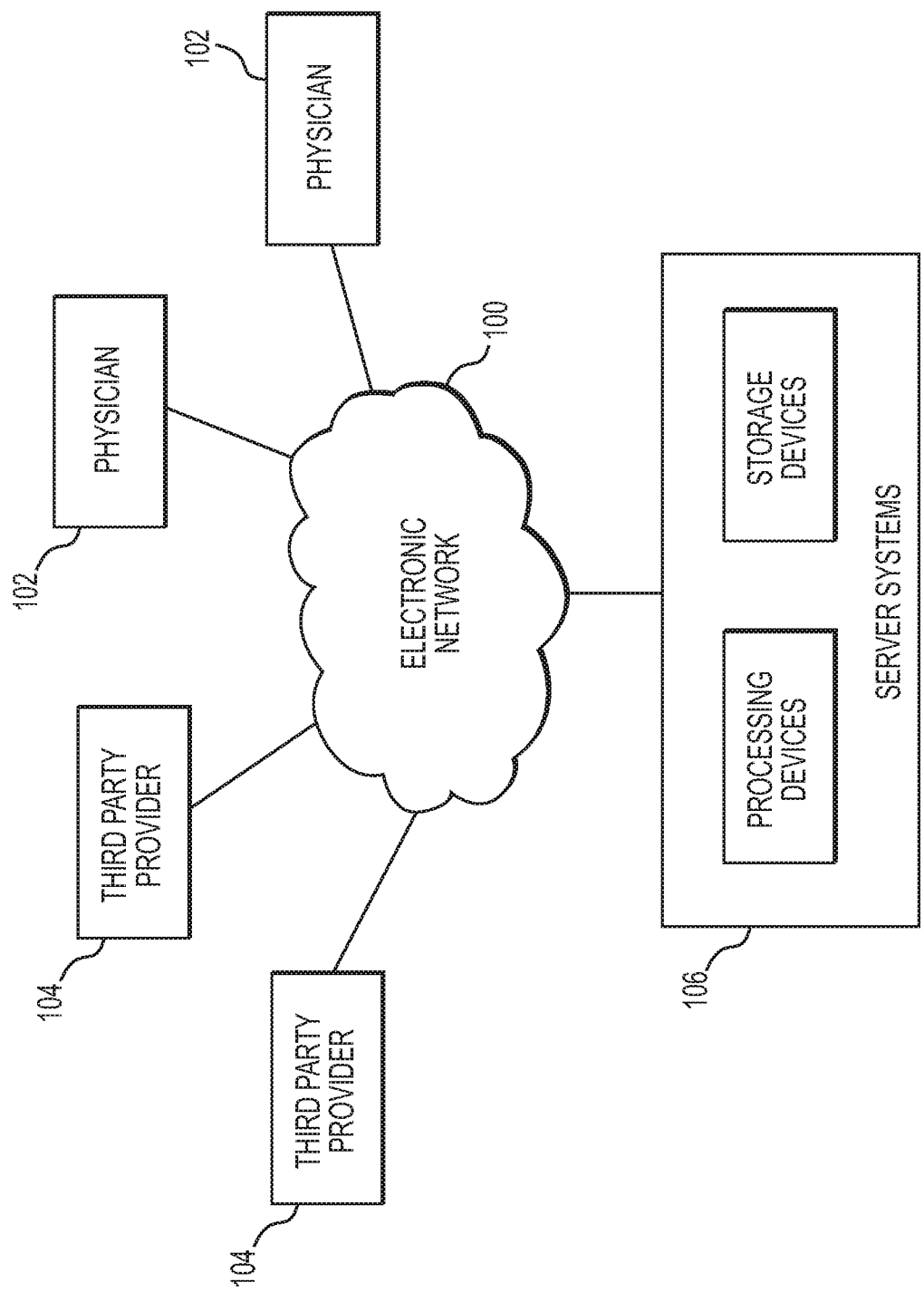
FIG. 1A is a block diagram of an exemplary system and network for manipulating image annotations, especially in validating and correcting automated image annotations, according to an exemplary embodiment of the present disclosure.

The present disclosure is directed to facilitating the creation of accurate models, for instance, models in preparation for computational analysis. Specifically, the present disclosure may include a guided workflow, by which users may be taken through multiple steps in order to validate a model. For example, an embodiment of the present disclosure may facilitate validating a segmentation used for modeling and simulation for blood flow of the heart (Taylor, Fonte, & Min, "Computational Fluid Dynamics Applied to Cardiac Computed Tomography for Noninvasive Quantification of Fractional Flow Reserve." Journal of the American College of Cardiology. 2013 Jun. 4; 61(22):2233-2241, the disclosure of which is incorporated herein by reference in its entirety). Segmentations for such modeling and simulation may involve an extremely precise image segmentation from a cardiac CT image to create a patient-specific 3D geometric model of the patient's heart. The present disclosure may guide users through automated image annotations, thus efficiently and effectively providing structure for trained users in validating and correcting the patient-specific 3D model to ensure reliability of the blood flow simulations and the correctness of the treatment decisions derived from the simulation. The process is designed to decrease analyst processing time, maintain or increase accuracy of computed flow reserve (FFRct) results, and improve reproducibility of measured fractional flow reserve (mFFR) results.

In other words, the method and systems for guiding a user through the image annotations may help analysts examine segmentation results (e.g., resultant image annotations from segmentation). The present disclosure involves a guided workflow for a user verifying a segmentation, for use in creating a segmentation for an image dataset. The term image annotation may generically represent any identification or indicia in an image (including, but not limited to, a 2D image, a 3D image or an image of greater dimension) that includes a localization or a labeling. Examples include: localization of particular points (landmarks), localization of lines and curves (e.g., diameters, centerlines), 2D regions of interest (a 2D segmentation), 3D regions of interest (a 3D segmentation), an n-D region of interest (an n-D segmentation), an n-D+time region of interest (an n-D segmentation tracked through time) or a labeling/classification of one or more identified structures or sections of the image (e.g. a label or score for each image in a time-series).

The present disclosure may include several methods for designing or directing workflows to assist analysts in the validation, or automating parts of the validation once there is a collective pool of analyst validation information.

In the following disclosure, each set of annotations may be associated with a validation "task." For example, aorta segmentation may be an "aorta task," identifying ostia points may be a "landmarks task," left ventricle myocardium segmentation may be during a "myocardium task," vessel labeling may occur during a "centerline labeling task", and vessel lumen segmentation may take place for a "segmentation task." In one embodiment, the workflow of the present disclosure may include an order or sequence for presenting each of the tasks. For example, the tasks may be presented in an order of dependency, where annotations that may govern or impact other annotations, may be presented earlier in the workflow. This way, subsequent annotations may be adjusted based on validations or corrections to their respective governing annotations. In other words, if one of the annotations with a dependency is modified by a user upon review, automated algorithms for consequent annotations may be re-run with the modified annotations as input.

In one embodiment, the tasks comprising the workflow of the present disclosure may include prompting review for red flags, then proceeding with prompting users with various validation tasks including, for example, tasks for validating an aorta, landmarks, myocardium, centerlines, centerline labeling, and segmentation. As a final task, a user may finalize the model. The dependency and ordering of the image annotations may be described in more detail by FIG. 1D.

It should be appreciated that any type of computing system, such as a computer having a digital memory storage device, a processor, and any desired user interfaces may be configured to perform the presently disclosed methods. Moreover, any type of servers, clustered computers, and/or cloud computers may be configured to perform the presently disclosed methods. Any of the above referenced devices may be connected to a network, such as the Internet, to receive and transmit data used in performing the presently disclosed methods.

Referring now to the figures, FIG. 1A depicts a block diagram of an exemplary system and network for validating and correcting automated image annotations. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of, for instance, one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 1B:
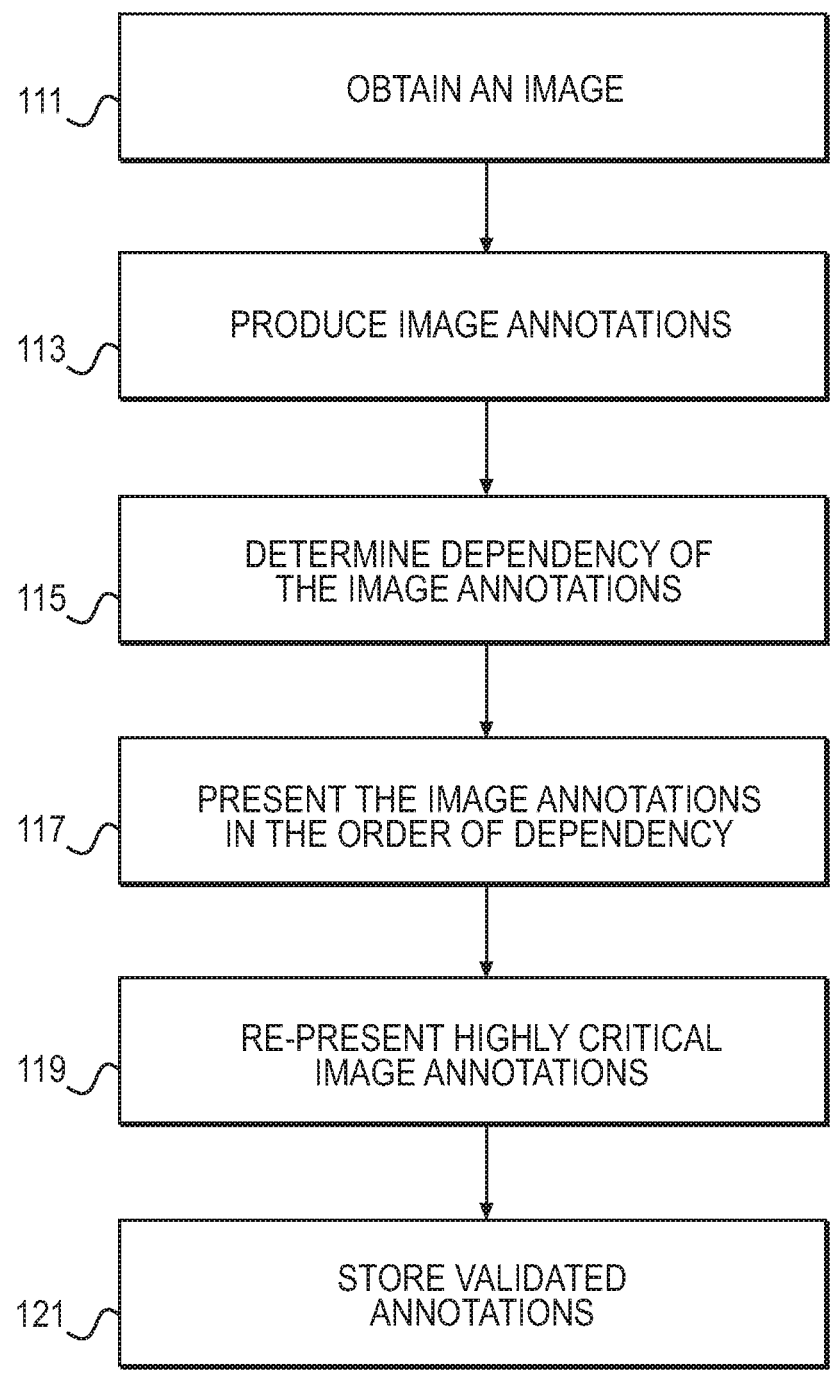
FIG. 1B is a block diagram of an exemplary method for validating and correcting automated image annotations, according to an exemplary embodiment of the present disclosure.

FIG. 1B is a block diagram of an exemplary method 110 for validating and correcting automated image annotations, according to an exemplary embodiment of the present disclosure. The method of FIG. 1B may be performed by server systems 106, based on information, images, and data received from physicians 102 and/or third party providers 104 over electronic network 100. In one embodiment, step 111 may include obtaining an image. For example, step 111 may include acquiring a digital representation (e.g., the memory or digital storage [e.g., hard drive, network drive] of a computational device such as a computer, laptop, DSP, server, etc.) of image data. In one embodiment, step 113 may include applying an automated image analysis system to produce a set of image annotations. Example automated image analysis systems include but are not limited to:

a. Face detection in a digital camera
b. Image or video labeling (tagging) in a collection of images/videos (e.g., YouTube)
c. 3D organ segmentation in CT medical images for radiation therapy planning
d. 2D left ventricle segmentation in ultrasound medical images for computing an ejection fraction
e. 2D cell detection in a microscopy image for image-based cytometry
f. 2D cell tracking through video in an optical microscopy image for determination of mitosis events
g. 3D tumor segmentation and feeder vessel centerline annotation in CT medical images for chemoembolization planning
h. 3D bone fracture segmentation in CT medical images for bone reconstruction planning
i. Tumor detection and segmentation in a digital mammography application In one embodiment, step 115 may include determining a dependency of the image annotations on each other, if any. For example, one or more image annotations may depend or hinge on other annotations. Put another way, one or more image annotations may affect or impact other annotations. In one embodiment, step 117 may include presenting, to a user, each annotation in order of dependency (e.g., an annotation is presented earlier if another annotation is dependent upon it). In some instances, a subset of annotations may be presented, for example, based on its need for user validation. In other words, step 117 may include refraining from presenting a group of annotations. Refraining from presenting an annotation may occur in cases where an automated image analysis reports high confidence in the automated annotation correctness or in cases where the annotation is of low importance, for instance. In one embodiment, step 117 may include determining which annotations to present or not present. For each annotation, step 117 of presenting an annotation to a user may include providing one or more visualizations of the annotation and/or supporting image data that allows the user to view and validate the annotation. The visualizations may or may not allow interactive interrogation from the user. Presenting annotations in step 117 may further include providing tools that enable the user to modify the annotation to achieve a quality meeting the user's satisfaction. Step 117 may still further include allowing a user to accept the annotation as validated before proceeding to the subsequent annotation. In some cases, step 117 may also include detecting modifications to annotations, made in the annotation visualizations (e.g., via the tools). In such situations, the dependent annotations may be recomputed. For example, the re-computing may be performed automatically. In some cases, already validated annotations may not be subject to the re-computing.

In one embodiment, step 119 may include determining one or more annotations as being highly critical to an application. Step 119 may further include re-presenting such annotations to a user or presenting such annotations to one or more additional users for validation. The determination of "highly critical" status may be performed in many application-specific ways (e.g. including, but not limited to, aspects of the annotation comprising, size, shape, appearance, density, spatial or other relationship to other annotations). For example, the annotations determined to be highly critical may be presented and reviewed by:

a. The user for a second time
b. A supervisor
c. Another expert
d. A panel of other individuals
e. As part of a training exercise to ensure reproducibility Step 121 may include storing or saving validated annotations to an electronic storage medium (e.g., hard drive, computer RAM, network communication channel).

Figure 1C:
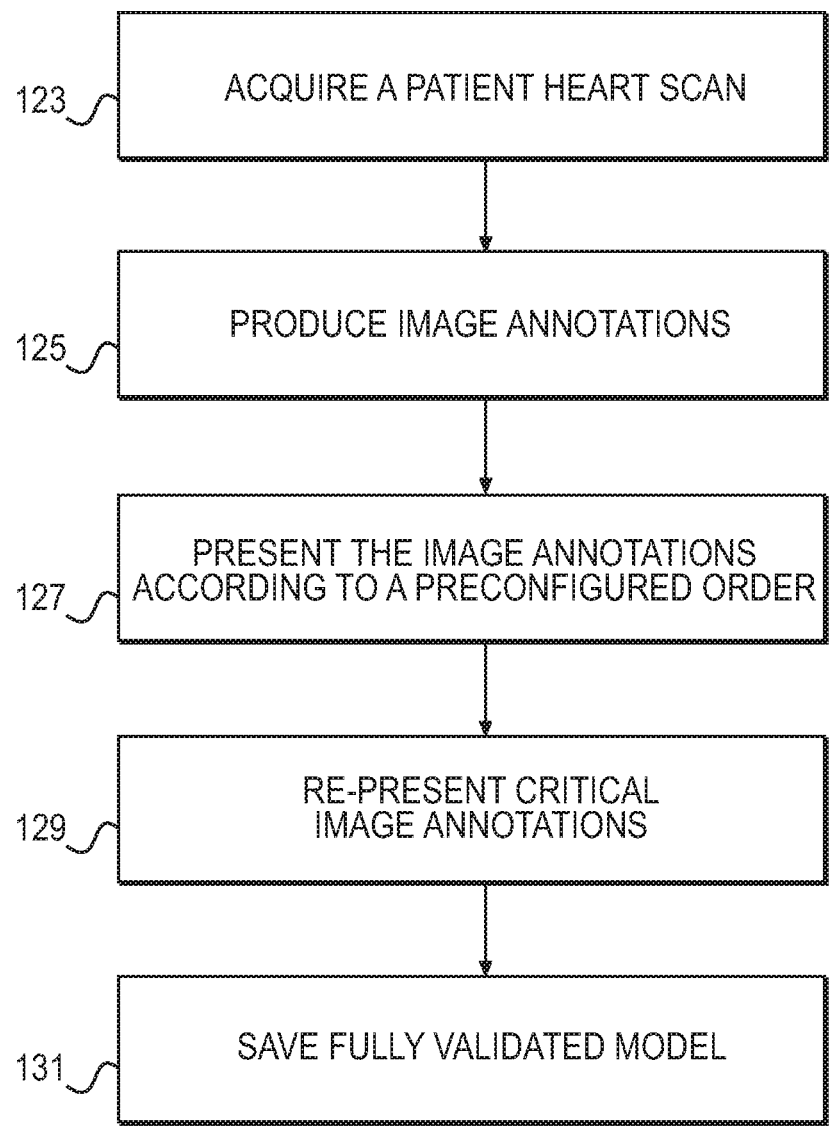
FIG. 1C is another block diagram of an exemplary method for validating and correcting automated image annotations, according to an exemplary embodiment of the present disclosure.

FIG. 1C is another block diagram of an exemplary method 120 for validating and correcting automated image annotations, according to an exemplary embodiment of the present disclosure. The method of FIG. 1C may be performed by server systems 106, based on information, images, and data received from physicians 102 and/or third party providers 104 over electronic network 100. Method 120 may serve as a specific embodiment of method 110.

A specific embodiment of the previously described system and method may include a blood flow simulation and determination of a simulated fractional flow reserve. The present disclosure is directed to using an automated image analysis system to generate a 3D patient-specific model (segmentation) of the vascular geometry (aorta and coronaries), a labeling of the coronary vessels, a 3D patient-specific model (segmentation) of the left ventricle myocardium, and an aortic valve point.

In one embodiment, generating the 3D model may begin with step 123 of acquiring a digital representation (e.g., the memory or digital storage [e.g., hard drive, network drive] of a computational device such as a computer, laptop, DSP, server, etc.) of a patient's heart scan (a 3D cardiac CT image). In one embodiment, step 125 may include the automated image analysis system applying image annotations to the model or images associated with the model. Specifically, the system may automatically annotate the following: a 3D segmentation of the aorta (e.g., using (Kirisli, et al., "Fully automatic cardiac segmentation from 3D CTA data: a multi-atlas based approach," Proceeding of SPIE. Vol. 7623, 762305-9, 2010), the disclosure of which is incorporated herein by reference in its entirety), the location of ostia points (e.g., using (Zheng, et al., "Efficient Detection of Native and Bypass Coronary Ostia in Cardiac CT Volumes: Anatomical vs. Pathological Structures," Proc. Intl Conf. Medical Image Computing and Computer Assisted Intervention, 2011) the disclosure of which is incorporated herein by reference in its entirety), the location of the aortic valve point (e.g., using (Zheng, Barbu, Georgescu, Scheuering, & Comaniciu, "Four-Chamber Heart Modeling and Automatic Segmentation for 3D Cardiac CT Volumes Using Marginal Space Learning and Steerable Features," IEEE Transactions on Medical Imaging, Vol. 27, No. 11, pp. 1668-1681, 2008), the disclosure of which is incorporated herein by reference in its entirety), coronary vessel centerlines (e.g., using (Kitamura, Li, & Ito, "Automatic coronary extraction by supervised detection and shape matching" International Symposium on Biomedical Imaging (ISBI), 2012 9th Institute of Electrical and Electronics Engineers (IEEE) International Symposium on May 2-5 2012), the disclosure of which is incorporated herein by reference in its entirety), labeling of the vessel centerlines by vessel name (i.e., right coronary artery (RCA), left anterior descending artery (LAD), left circumflex artery (LCX), where this labeling may be performed by using a set of training labels to determine the statistics of the geometric positioning of each labeled vessel centerline and assigning the vessel centerline the labels having the maximum likelihood based on its geometric position (see e.g., (Lorenz & Berg, "A Comprehensive Shape Model of the Heart" Medical Image Analysis, vol. 10, no. 4, pp. 657-670, (18 May 2006), the disclosure of which is incorporated herein by reference in its entirety), 3D segmentation of the coronary vessel lumen (e.g., using (Schaap, et al. "Robust Shape Regression for Supervised Vessel Segmentation and its Application to Coronary Segmentation in CTA" IEEE Transactions on Medical Imaging, Vol. 30, No. 11, November 2011), the disclosure of which is incorporated herein by reference in its entirety), 3D segmentation of the left ventricle myocardium (e.g., using (Kirisli, et al., 2010)), etc. In other words, step 127 may include presenting image annotations to a user in the order:

a. Aorta segmentation
 b. Ostia points
 c. Aortic valve point
 d. Left ventricle myocardium segmentation
 e. Coronary vessel centerlines
 f. Vessel labeling
 g. Vessel lumen segmentation Such an order may show a dependent relationship among image annotations. If one of the annotations with a dependency is modified by a user upon review, the automated algorithms for consequent annotations may be re-run with the modified annotation as input.

Following a completely validated segmentation, step 129 may include analyzing the lumen segmentation for critical regions. For example, step 129 may include finding critical regions by determining areas where diameter reduction exceeds 50%. Any lumen segmentation components that are marked critical may be presented again to the user for a second examination and modification, if necessary. In one embodiment, step 131 may include saving a fully validated model (including any modifications) to an electronic storage medium (e.g., hard drive, computer RAM, network communication channel).

Figure 1D:
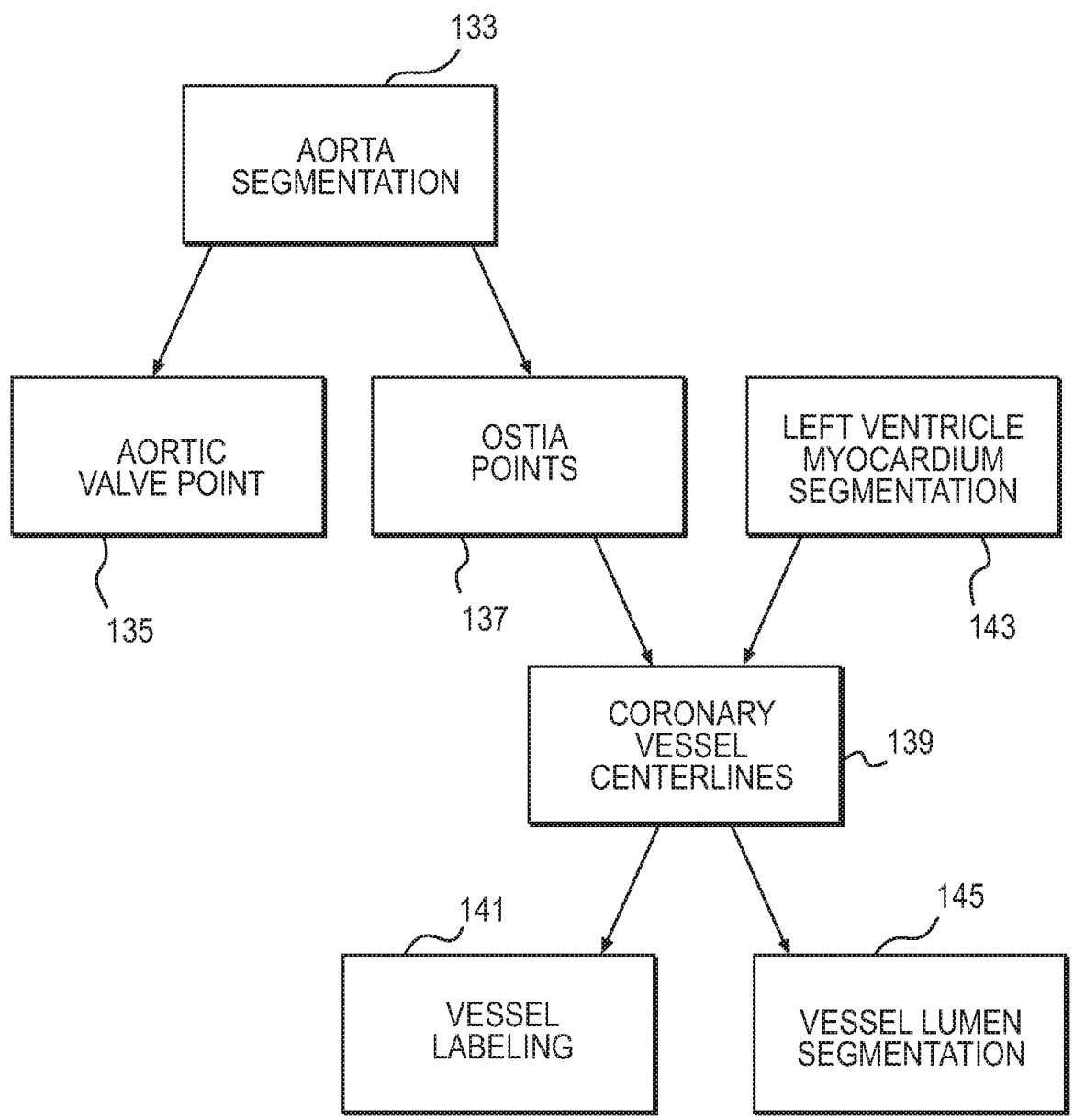
FIG. 1D is a diagram of an exemplary series of dependencies for validating and correcting automated image annotations, according to an exemplary embodiment of the present disclosure.
Figure 3A:
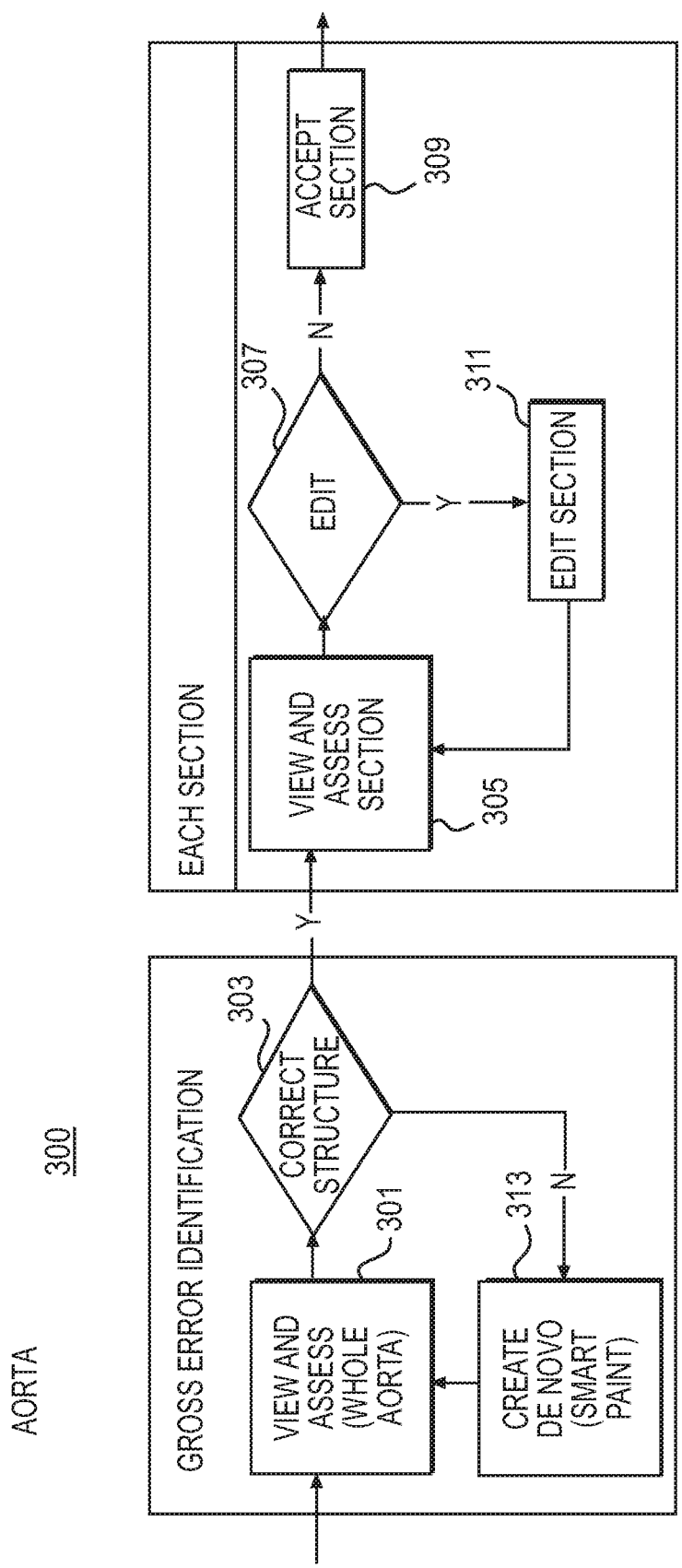
FIG. 3A is a block diagram of an exemplary aorta task, according to an exemplary embodiment of the present disclosure.

FIG. 1D is a diagram of an exemplary series of dependencies 140 for validating and correcting automated image annotations, according to an exemplary embodiment of the present disclosure. For example, aorta segmentation 133 (e.g., detailed in FIG. 3A showing aorta task 300) may serve as a starting point. Subsequent validation steps may depend on the aorta segmentation 133. Following aorta segmentation 133, a workflow may present steps relating to an aortic valve point 135 and/or ostia points 137 (e.g., corresponding to landmarks task 400 shown in FIG. 4A). The next steps may relate to left ventricle myocardium segmentation 143 (e.g., myocardium task 500 of FIG. 5A). A subsequent dependent task may include analysis of coronary vessel centerlines 139 (e.g., shown in centerlines task 600 of FIG. 6). From the workflow steps relating to coronary vessel centerlines 139, the workflow may lead a user to vessel labeling 141 or vessel lumen segmentation 143 (e.g., lumen task 700 of FIG. 7A). This chain of dependencies in tasks may guide a user through a predictable, logical series of validation steps towards building a complete model.

As previously discussed, annotations may be presented via one or more visualizations. In one embodiment, each visualization of the annotations may include tools to help complete the validated segmentation. For example, "Smart Paint" and "Nudge" tools may be used across a workstation, for any task that utilizes a segmentation. Specific functionality for the different tasks or modes may differ, but the underlying principle of the tool may be consistent across the different tasks.

For example, Smart Paint may operate by adding "inside" (or "object") and "outside" (or "background") seeds to the image data. The smart paint algorithm may generate a new segmentation using these seeds and possibly any existing segmentation information. The smart paint algorithm may use a version of the random walker algorithm for segmentation. In some cases, the user may add a minimal number of seeds to obtain a good segmentation. Ultimately, with enough paint, a user may obtain any segmentation. Smart Paint may function on the MPRs and add paint in a disc-like shape. Further, the size of a brush for Smart Paint may be adjustable. In one situation, a size of the brush may increase when a user scrolls up on a mouse wheel, and decrease in size when the user scrolls down on the mouse wheel. Furthermore, seeds may be erased (e.g., using an Erase Seeds tool that may erase both inside and outside seeds). If a user paints over an existing seed with a seed of an opposite type, the original seed may be overwritten.

For an edit mode for an aorta task and myocardium task, Smart Paint may update the segmentation with each addition or subtraction of inside or outside seeds. The algorithm may operate using a current segmentation. The smart paint algorithm may update segmentation in a region of interest (ROI) around a currently added paint stroke.

For a create mode for an aorta task and myocardium task, Smart Paint may update the segmentation only when prompted with a button click. In some cases, the algorithm may incorporate all paint to create a new segmentation, rather than use the current segmentation. The algorithm may use all paint strokes to define a ROI within which to work.

For a lumen mode, Smart Paint may affect segmentation in neighboring un-reviewed or reviewed sections. The segmentation may update with each placement of seeds, using the current segmentation as a starting point. The algorithm may update the segmentation in a ROI around a currently added paint stroke, but incorporate all seeds contained within the ROI.

Regarding the Nudge tool, Nudge may operate by pushing segmentation in a direction of mouse movement, with a spherical shape centered at a mouse cursor. If a user starts pushing a segmentation while inside a segmentation visualization, the edit may be referred to as an "Inside Nudge." If the user starts the pushing segmentation when outside the segmentation, the edit may be referred to as an "Outside Nudge." The size of the nudge may be determined by a distance between the cursor and the segmentation. The further away the cursor, the larger the edit. Nudge may affect the segmentation directly, so this tool may work in real time.

In one embodiment, Nudge may work in MPR views. In a further embodiment, Nudge may be available in aorta edit mode 340 (e.g., shown in FIG. 3C), myocardium edit mode 540 (e.g., shown in FIG. 5C), and lumen task 700. Functionality between the three may be very similar, with unique variations for the myocardium and lumen applications. For myocardium edit mode 540, an inner and outer contour may exist since the segmentation may only pertain to the left ventricular muscle. Thus, edits within the muscle that either push the outer contour outwards or the inner contour inwards may be considered "Inside Nudges"; edits outside the segmentation that either push the outer contour inwards or the inner contour outwards, may be considered "Outside Nudges." For the lumen task 700, in order to minimize switching sections and creating segmentation cusps, Nudge may work on different contours and sections. In some cases, Nudge may not operate on contours of distal sections, or on contours of branch vessels. However, Nudge may operate on contours of the proximal or connecting branch. This way, users may use the tools to modify the bifurcation of both contours only on the branch section. On a parent vessel section, Nudge may affect the parent vessel section and leave a branch contour untouched.

FIG. 2 is a block diagram of an exemplary red flags task 200, according to an exemplary embodiment of the present disclosure. Red flags task 200 may be performed by server systems 106, based on information, images, and data received from physicians 102 and/or third party providers 104 over electronic network 100. In one embodiment, the purpose of red flags task 200 may be to confirm the selection of a series of images from which to create a model. For example, where a model may include modeling lumen and myocardium, red flags task 200 may be the first opportunity for a user to review data in detail and determine adequacy of images for processing into a model. In addition, red flags task 200 may help users make note of any anatomical anomalies apparent from the series. FFRct may include several contraindications that may prevent its use in certain patient anatomical anomalies, diseases, or in certain CT acquisition issues. As such, it is helpful to review FFRct data for appropriateness prior to processing. Red flags task 200 may methodically present a user with each contraindication to verify that the patient and/or data is appropriate for processing. In some cases, a user may determine the appropriateness of the selection of the series for processing but leave an automatic determination unchanged unless a serious error in the calculation is observed.

In one embodiment, red flags task 200 may include step 201, where a user may view and assess a series of images. For example, a user may be assessing a series of images for images that best show a lumen. In one embodiment, step 201 may include red flags task 200 presenting a single multiplanar reconstruction (MPR) with constrained navigation, a user interface (UI) element for series selection, a list of acceptable image quality and/or patient quality elements, an exemplary image of a pathology or anomaly to be assessed, and UI elements to mark particular pathology and/or anomaly as fit for acceptance or rejection. In one embodiment, an MPR view may include image data intersected by a plane through the image volume. More specifically, an MPR view may include an axial MPR view (e.g., in the traverse plane). For example, the MPR view may be set to a default zoom and centering point; and an automatic window/level may be applied. In one embodiment, a window may include a view shown at a workstation visualization, including a zoom level. A level may include an orientation or alignment of a view. Further, the MPR view may be oriented so that the anterior direction is towards the top of the screen. In one embodiment, an MPR view may include scrolling and windowing capabilities. In one embodiment of the red flags task 200, rotation, zoom, and panning may not be available. This is so that focus may be kept at global red flag issues. Rotation, zoom, and panning capabilities may be included as navigation options once a set of images or image annotations is already deemed acceptable for analysis and use.

In one embodiment, a user is initially presented with an axial MPR as a default view, and a single example image of the pathology to be reviewed. The user may be tasked with reviewing image data for the particular item. For example, step 203 of searching for red flags may include reviewing image data for inadequacies. The user may be prompted or provided with tools to mark the item as acceptable or rejected, depending on whether an item presented prevents the series from being used for processing. If a user marks an item as acceptable, the red flags task 200 may bring up the next item in the series for review. If an item is marked as rejected, the workstation may automatically close and the case may be recorded as rejected. In one embodiment, a task manager may be displayed to present the user with further options, for instance, the option to select another series to review, to return to an earlier item in a series, to see all available series' including a list of accepted and rejected series, etc. The user may review each item for an incorrect data list and anomaly list. As each item is marked as accepted, a list of anomalies may be populated and marked as accepted. In one embodiment, red flags task 200 may determine that a user has either accepted or rejected a series (step 205).

If a second series is selected for processing (i.e., different series are selected for lumen and myocardium processing), the second series may also be reviewed for appropriateness. For example, a user may be prompted to follow through step 207 of viewing and assessing an image in the second series, step 209 of searching for red flags, and accepting and/or rejecting the image (step 211). In one embodiment, a user may be presented with each item sequentially. The user may then mark each item on two image quality lists (e.g., an incorrect data list and an anomaly list). On the acceptance of the last item in the list, the next task, the aorta task, may be activated. If an item is rejected at any point, an entire series or set of annotations associated with a patient may be rejected. In one embodiment, the workstation may automatically close. In another embodiment, the user may be presented with the next series (e.g., the first item of the next series) or a menu from which the user may select a series. In one embodiment, red flag task 200 may only have one mode, so mode switching options may be unnecessary.

In cases where incorrect data may be selected for processing, remaining data sent by a sampling or test site may still be appropriate for processing. For example, red flags task 200 may include a determination of whether all the series available have been analyzed (step 213). Where more images and/or series are available, steps 207, 209, and 211 may be repeated for images in another series. If all series have been analyzed, red flags task 200 may note an error (step 215).

In one embodiment, red flags task 200 may be available for a user to return to, should a user notice an anomaly in later stages of processing. For example, a workflow may include a red flags tab that may return a user to red flags task 200. Red flags task 200 may then present a user with each anomaly for review. If the user invalidates a series at this point, the red flags task 200 may note the series as rejected and close the workstation.

In one embodiment, red flags task 200 may include a progress bar overlaying a task name. The progress bar may only be visible when a user is presently undergoing the red flags task 200. Each item that must be reviewed may take up an equal portion of the task bar. Therefore, if two series are selected for processing, items for a single series may fill up half of the progress bar. In addition, a UI may include a list of anomalies. The list may be selectable by users and selections (of lack of selections) may be changed if anomalies are detected at a later stage.

FIG. 3A is a block diagram of an exemplary aorta task 300, according to an exemplary embodiment of the present disclosure. Aorta task 300 may be performed by server systems 106, based on information, images, and data received from physicians 102 and/or third party providers 104 over electronic network 100. In one embodiment, aorta task 300 may lead a user through segmenting an aorta. In a further embodiment, aorta task 300 may proceed towards the next task only after a user accepts some aorta segmentation. In one embodiment, aorta task 300 may further include calculating an aorta centerline. The aorta centerline may be used in a "Finalize" sub-task to calculate aorta inlet and outlet boundary condition planes. In one embodiment, aorta task 300 may include three modes: inspect, edit, and create. Each mode may have a set of views and tools to assist in the inspection, modification, and/or creation of the aorta segmentation. In one embodiment, aorta task 300 may be divided into two components: gross error identification and section analysis. Gross error identification may allow a user to look generally at the structure of the entire aorta, while section analysis may include more detailed analysis. In one embodiment, step 301 may include viewing and assessing the entire aorta. For example, step 301 may include presenting a user with the gross structure of an aorta. Next, step 303 may permit a user to correct the structure of the aorta. In one embodiment, the intention for aorta task 300 may be that a user may determine the appropriateness of the selection of the series for processing, but leave the automatic determination unchanged unless a serious error in the calculation has occurred. Various embodiments of step 303 may encompass various thresholds for what constitutes a "serious error" that may warrant correction. Selecting to correct a structure of the aorta, may trigger steps 305-311 of section analysis. For example, step 305 may permit a user to view and assess each section. Then, step 307 may permit a user to edit a section. After editing, a user may be prompted to accept the section (step 309). Alternately, a user may continue to edit a section (step 311). In one embodiment, accepting the section may permit the user to return to step 301 of global analysis of the aorta before selecting another part of the aorta image to correct. In another embodiment, step 309 of accepting the section may bring an end to the aorta task 300 and permit a user to go onto the next task, the landmarks task 400.

In another embodiment, gross error identification of aorta task 300 may further include the option to create a portion of the aorta (step 313), rather than correcting each section. Step 313 may include using a "paint" function to draw a portion of the aorta, de novo. Step 313 may occur where issues with the aorta segmentation are so great, creating the segmentation anew may be preferable to editing a previous segmentation.

Figure 3B:
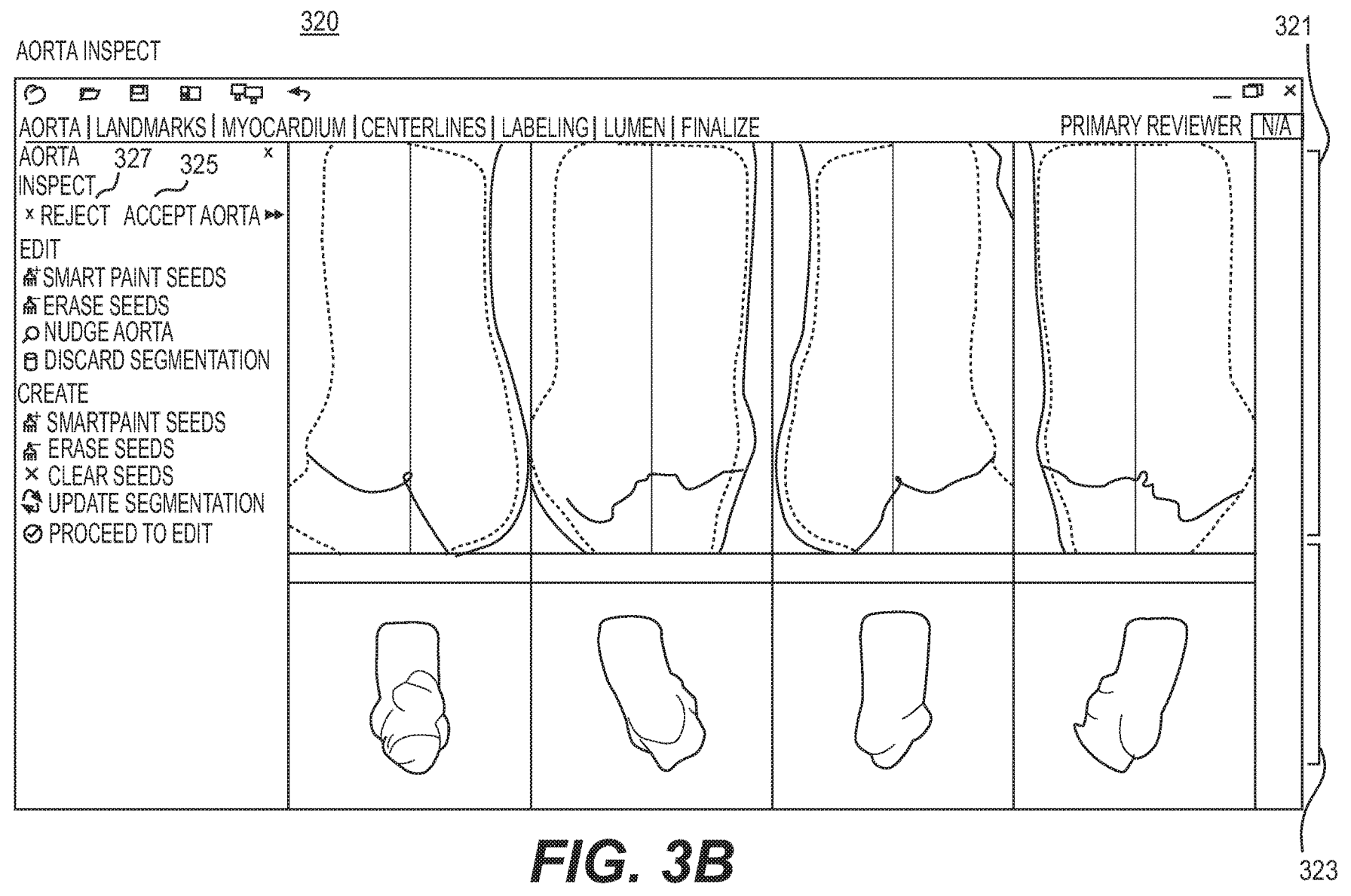
Figure 3C:
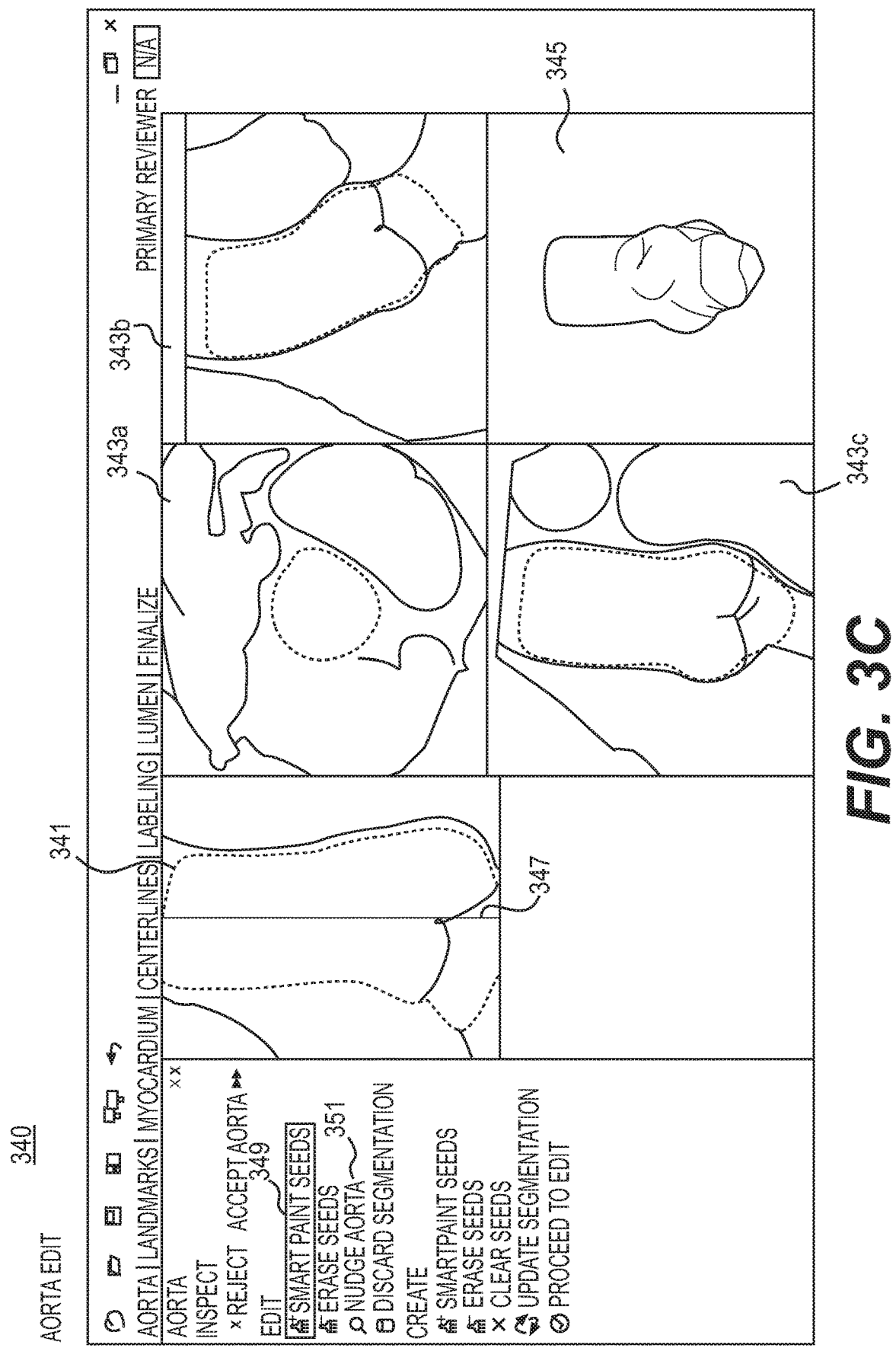
FIG. 3C is a display of an aorta edit mode, according to an exemplary embodiment of the present disclosure.
Figure 3D:
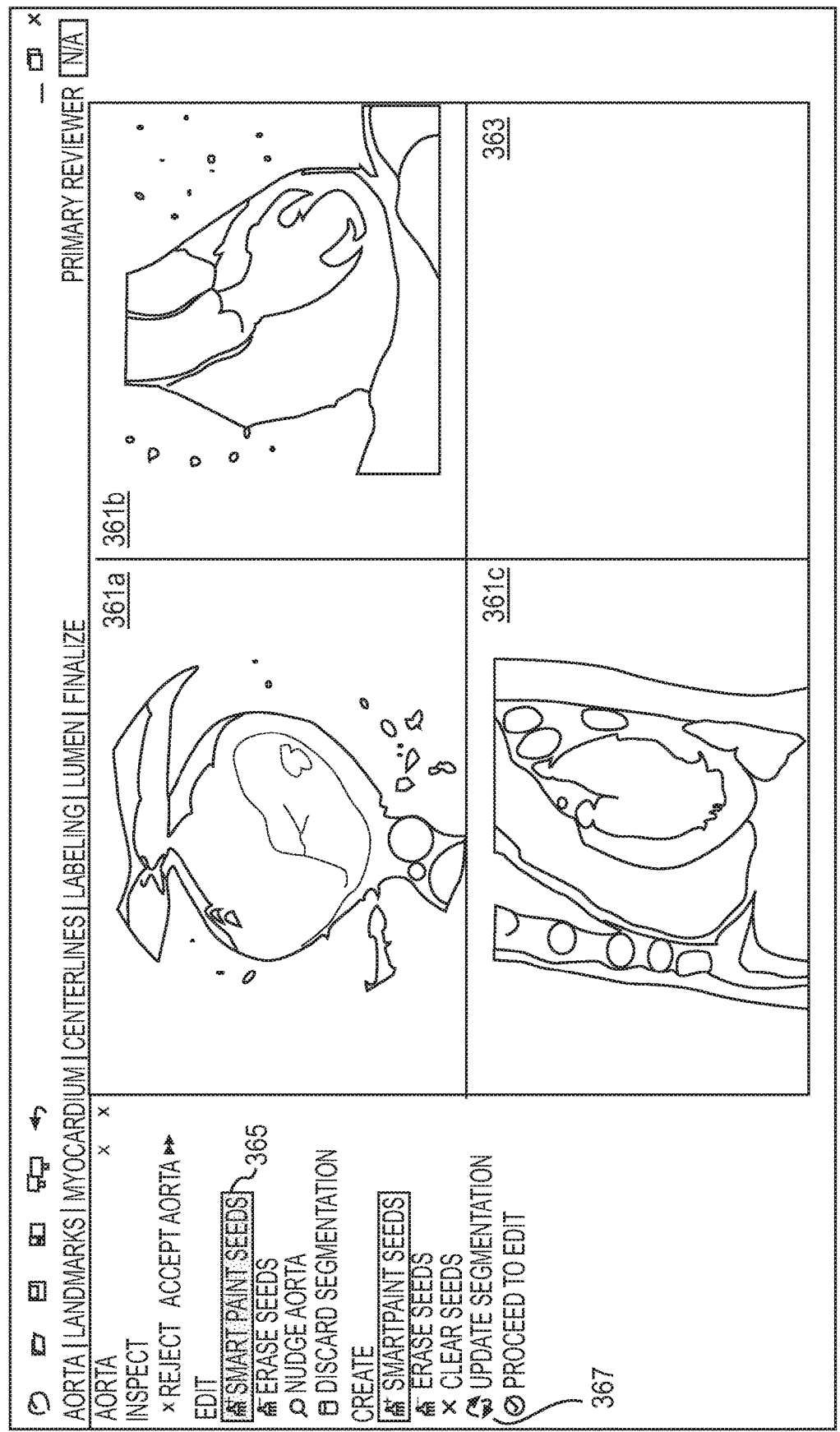
FIG. 3D is a display of an aorta create mode, according to an exemplary embodiment of the present disclosure.

FIGS. 3B-3D depict exemplary interfaces by which a user may inspect an aorta, segment the aorta, and calculate an aorta centerline. The user may selectively Inspect, Edit, and Create aorta segmentation using exemplary interfaces of FIGS. 3B-3D, respectively. Each mode may include a set of views and tools to assist in the inspection, modification, or creation of the aorta segmentation. The available tools at this point may include "Accept Aorta" and "Reject Aorta." Selection of "Accept Aorta" may cause the process to move to the next task, landmarks task 400. Selection of "Reject Aorta" may enable aorta edit mode (e.g., shown in FIG. 3C). In one embodiment, aorta task 300 may include a progress bar overlaying the task name (e.g., Inspect, Edit, and Create). For example, the progress bar may only be visible when a user is undergoing aorta task 300. In a further embodiment, progress for the aorta task 300 may be binary: all or nothing. In other words, the progress bar may be empty when the segmentation is not accepted and 100% when the task is completed. For such an embodiment of a progress bar, the 100% status may only be seen when navigating back to the aorta task 300 from another task.

FIG. 3B is a display of an aorta inspect mode 320, according to an exemplary embodiment of the present disclosure. Aorta inspect mode 320 may be used to quickly determine whether gross segmentation of the aorta generated by automatic algorithms is fit to proceed with processing, or whether the generated aorta requires modification. In one embodiment, the aorta inspect mode 320 may have a layout that includes multiple images from straightened curved planar reformations (sCPRs) and several images from iso-surfaces (ISOs). sCPRs may include displays of image data of an entire length of a tubular structure in a single view. For example, sCPRs may include using a straightened representation of the structure's centerline. A centerline of the structure may be needed to generate this view. In some cases, the sCPRs may be based on curved planar reformations (CPRs). ISOs may include displays of a 3D representation of a signed distance field (SDF) of a current segmentation.

In one embodiment, one form of aorta inspect mode 320 may include four sCPRs 321 and four ISOs 323, arranged such that the ISOs 323 are below the sCPRS 321. In one embodiment, the sCPRs 321 may be constructed by the aorta inspect mode 320 using an aorta centerline generated from automatic algorithms. An sCPR 321 may be oriented such that a superior direction is towards the top of a screen. The sCPRs 321 may then be rotated to show 0°, 45°, 90°, and 135° planes. The sCPRs 321 may be centered such that the top (first point) of an aorta centerline is located at the top border of a view. Zoom level for all sCPRs 321 in the aorta inspect mode 320 may remain at the same level. The sCPRs 321 may be zoomed such that a "radius" of the segmentation (and buffer regions) may be shown in the view. The sCPRs 321 may also be auto-window and/or leveled, wherein aorta intensity may be used to calculate the appropriate window and level.

In one embodiment, the ISOs 323 may also be oriented such that the superior direction is situated towards the top of the screen. The ISOs 323 may be rotated to show 0°, 90°, 180°, and 270° planes. The ISO 323 may be centered such that the centroid of the aorta segmentation is at a center of the view. In one embodiment, zoom level for all ISOs 323 may be at the same level. In a further embodiment, the ISO 323 may be zoomed such that the radius of the segmentation (and buffer region) may be shown in the view. In one embodiment, navigation may be disabled for all views because the views for aorta inspect mode 320 may be designed to allow users to evaluate aorta segmentation "at-a-glance," thus allowing a reproducible binary decision for acceptance. Navigation may be unavailable for aorta inspect mode 320, in one embodiment, to facilitate a reproducible binary decision for acceptance. Fine details may not be critical for aorta segmentation and are therefore not emphasized in aorta inspect mode 320.

In one embodiment, aorta inspect mode 320 may include available tools Accept Aorta 325 and Reject Aorta 327. A selection of Accept Aorta 325 may cause continuation to the next task, landmarks. Selection of Reject Aorta 327 may enable aorta edit mode 340.

FIG. 3C is a display of an aorta edit mode 340, according to an exemplary embodiment of the present disclosure. Aorta edit mode 340 may be used to provide tools, views, and navigation capabilities to assist in a quick and reproducible modification of aorta segmentation. In one embodiment, aorta edit mode 340 may include one sCPR 341, three images from multi-planar rendering (MPR) 343a-343c (or MPRs 343), and an ISO view 345. In one embodiment, the sCPR 341 may be located at the left of the screen as a reference, while the other four views share the rest of a screen space in a 2×2 configuration, with the ISO 345 in a bottom right corner. The sCPR 341 may be constructed using an aorta centerline generated from automatic algorithms. In one embodiment, the sCPR 341 may be oriented such that a superior direction is towards the top of the screen. The sCPR 341 may be centered such that the top (e.g., first point) of the aorta centerline is located at the top border of the view. The sCPR 341 may be zoomed such that the "radius" of the segmentation (plus buffer) may be shown in the view. The sCPR 341 may also be auto-window and/or leveled, wherein aorta intensity may be used to calculate an appropriate window and level.

In one embodiment, the MPRs 343 may be constrained to move and rotate based on the aorta centerline. MPR 343a may include a cross-sectional view; MPR 343b may include a lateral view, and MPR 343c may include a longitudinal view. The lateral MPR 343b and longitudinal MPR 343c may be oriented such that the superior direction is towards the top of the screen. The cross-sectional MPR 343a may have an orientation initially set to synchronize with the longitudinal MPR 343c. The MPRs 343 may be centered around an aorta centerline point. In addition, zoom may be fixed and kept consistent across all the MPRs 343. In one embodiment, the MPRs 343 may share the same window and/or level as the sCPR 341.

In one embodiment, the ISO 345 may be initially oriented such that the superior direction is towards the top of the screen. The ISO 345 may be centered, such that a designated center of aorta segmentation is positioned at the center of the view. In one embodiment, the ISO 345 may be zoomed such that the radius of the segmentation (along with the buffer region) is shown in the view.

In one embodiment, the aorta edit mode 340 may include constrained navigation. Alternatively or in addition, the aorta edit mode 340 may stem mostly from an Inspector Gadget 347 located in the sCPR 341. For example, dragging the Inspector Gadget 347 up and down may re-center and pan all views of MPRs 343 such that centering points remain on the aorta centerline and the center point stays positioned at the center of the view. Similarly, dragging the Inspector Gadget 347 left and right may rotate all views of MPRs 343 and the sCPR 341. Rotation in the cross-sectional view and longitudinal views may occur around the aorta centerline. Rotation in the lateral view may occur around the transverse axis. 3D rotation, zooming, and panning may be available on the view of ISO 345.

Further, aorta edit mode 340 may include an exemplary interface by which a user may edit the aorta segmentation. Specifically, in one embodiment, aorta edit mode 340 may provide two sets of tools for editing: Smart Paint 349 and Nudge 351. While these tools may be used in various forms of functionality for different sections, aorta edit mode 340 may include specific behaviors for each tool. Smart Paint 349 may include two tools: inside seeds and outside seeds. Use of either of these tools may automatically update segmentation. For example, an update may occur in one second or less. An algorithm may use a most recent segmentation and use the additional seeds to modify the latest segmentation. In one embodiment, tools associated with Smart Paint 349 may work on MPRs 343. In one embodiment, the tool, Nudge 351, may also work on MPRs 343. Nudge 351 may permit users to move a seed a small degree. Updates from using Nudge 351 may be near real-time.

FIG. 3D is a display of an aorta create mode 360, according to an exemplary embodiment of the present disclosure. Aorta create mode 360 may be used to provide tools, views, and navigation capabilities to assist in creation of aorta segmentation. The aorta create mode 360 may be triggered where an algorithm produces a segmentation that misidentifies the aorta or produces large errors that would be inconvenient to resolve in the myocardium edit mode 540 described in FIG. 5C. In one embodiment, the aorta create mode 360 may include three MPRs 361a-361c (or MPRs 361) and an ISO 363 arranged in a 2×2 layout. In one embodiment, the MPRs 361a, 361b, and 361c may initially show the transverse, coronal, and sagittal planes, respectively. The MPRs 361 may be centered at the center of the volume of the image shown. The MPRs 361 may be set to a default zoom such that the image volume fills one of the views. In one embodiment, the three MPRs 361 may have the same window and/or level, set to an automatic preset. In this embodiment, the three MPRs 361 may share a centering point, zoom, and wind and/or level. Rotation may be synchronized between the three MPRs 361 such that the planes being displayed at any time are always orthogonal.

In one embodiment, the ISO 363 may initially be blank when entering aorta create mode 360, but the ISO 363 may populate as an aorta segmentation is generated. The ISO 363 may be oriented such that the superior direction is towards the top of the screen. In one embodiment, the ISO 363 may be centered such that the "center" of the aorta segmentation is at the center of the view. The ISO 363 is zoomed such that the radius of the segmentation (including a buffer region) is shown in the view.

In one embodiment, the aorta create mode 360 may include full navigation, meaning users may rotate, pan, re-center, reset orientation, zoom, and adjust a window and/or level on any MPR 361. In one embodiment, aorta create mode 360 may include the tool, Smart Paint 365. Segmentation may occur when a user selects a button, Update Segmentation 367. In one embodiment, segmentation may re-calculate based on seeds from Smart Paint 365. For example, if segmentation is based only on seeds from Smart Paint 365, aorta create mode 360 may discard the initial segmentation. The update may therefore take longer than Smart Paint 349 of the aorta edit mode 340. In one embodiment, Smart Paint 365 and Update Segmentation 367 may only work on the MPRs 361.

In combination, the aorta inspect mode 320, aorta edit mode 340, and aorta create mode 360 may be used in the following manner. When the aorta task 300 is enabled, a user may use sCPRs to view segmentation results. At this stage, the user may be watching for whether aorta segmentation is high enough up the ascending aorta. The user may also look for whether a valve point is sufficiently covered by the segmentation. Further, a user may observe whether ostia are visible in sCPRs. In one embodiment, volume rendering (VR) images may be used to support the decisions. For example, VR images may display a 3D projection of a 3D data set. One such case may include a VR display mapping intensity to opacity and color, using a transfer function. If an aorta is deemed acceptable, a user may select "Accept Aorta" (e.g., Accept Aorta 325 of FIG. 3B) and move on to the landmarks task 400.

If the user desires clarification or if the user observes a problem in the segmentation, the user may enable the aorta edit mode 340 by selecting "Reject Aorta" (e.g., Reject Aorta 327 of FIG. 3B) to trigger the aorta edit mode 340, associated with steps 307 and 311 of aorta task 300. In the aorta edit mode 340, a user may navigate on the sCPR 341 or rotate the MPRs 343 to view segmentation and again evaluate if the segmentation is complete. In one embodiment, Smart Paint 349 may be used to first modify segmentation as close as possible to desired segmentation. Edits using Smart Paint 349 may affect a local section of the aorta segmentation, and using both inside and outside seeds may help define a better segmentation. Smart paint 349 may be used to make larger edits, while minor edits to segmentation may be completed using Nudge 351. Both Smart Paint 349 and Nudge 351 tools may operate in a three dimensional context, so a user may be reminded to scroll through image slices to check the effect of the tool. In one embodiment, a user may be prompted to verify ostial segmentation. For the ostial segmentation, the user may again, ask whether aorta segmentation is high enough up the ascending aorta, whether a valve point is included, etc. After edits are complete, a user may click "Accept Aorta," including Accept Aorta 325 of FIG. 3B.

In one embodiment, aorta create mode 360 may be the preferred mode for a scenario where edits to a segmentation cannot achieve a desired segmentation. For example, aorta create mode 360 may cause a discarding of the segmentation to clear a current segmentation and re-center images on the aorta (e.g., near the valve point). In one embodiment, a user may rotate a view so that the ascending aorta, valve point, and parts of the ostia are visible. A user may add inside and outside seeds to the view such that the extent of the aorta is covered by the inside seeds and the aorta is surrounded by outside seeds. In one embodiment, a user may select to rotate to a view so that it is almost orthogonal to a view and the same extent of aorta may be seen. The rotation may be done on yet another view, as the views may be constrained to be orthogonal. Again, inside and outside seeds may be added using the criteria above and the segmentation may be updated based on the new seeds. In one embodiment, these steps may be repeated as needed, using both inside and outside seeds such that all major features of the aorta are captured. When segmentation is complete, a user may return to aorta edit mode 340, if desired, to use the centerline from segmentation for navigation. In one embodiment, users may only return to aorta edit mode 340 to verify segmentation. Further edits may be discouraged at this point, as the segmentation may change in unexpected ways due to the discarding of original seeds in the aorta create mode 360. Where no further edits are desired, a user may select a button, for example, "Accept Aorta," and move onto the landmarks task 400.

In one embodiment, the aorta inspect mode 320 may be the initial mode when users open the workstation. Upon selecting "Accept Aorta," for example, a user may move to the next task. All aorta modes may include some form of an option for "Accept Aorta." As discussed earlier, aorta inspect mode 320 may only have two options: Accept Aorta and Reject Aorta. Selecting to eject an aorta may enable aorta edit mode 340. To move out of the aorta edit mode 340, users may select "Accept Aorta." If the aorta segmentation is not easily modifiable, users may select some form of "Discard Segmentation" to completely discard an existing aorta segmentation and activate the aorta create mode 360. In such a case, initial segmentation of the pipeline of images may not be reused. Segmentation may be recalculated according to creation or modification of segmentation. In one embodiment, users may also move on to a next task in the aorta create mode 360 by selecting a form of "Accept Aorta." If users wish to return to aorta edit mode 340 (e.g., to verify a created segmentation using the views and layout available in the aorta edit mode 340), users may select a button that may entail, for example, "Enable Edit Mode."

Regarding background calculations, any changes to aorta segmentation may impact downstream tasks. In aorta edit mode 340, Smart Paint 349 or Nudge 351 may cause segmentation to exclude an ostium candidate or accepted ostium. In such a situation, the ostium point may be deleted. If the candidate was an accepted ostium, a warning message may appear reminding the user of the status of the ostium point. In one embodiment, an aorta centerline may not be recalculated if edits are done in the aorta edit mode 340.

In one embodiment, selecting aorta create mode 360 may automatically delete all previous calculations, and the segmentation may be recalculated with every update in segmentation made in aorta create mode 360. Upon acceptance of an aorta segmentation in aorta create mode 360, an aorta centerline may be recalculated and used for the next task (e.g., landmarks task 400) and for boundary condition generation.

In one embodiment, users may select to return and/or re-enable the aorta task 300 from any other task. In one embodiment, to return to any of the aorta tasks 320-360 from any other task, an initial mode for display may be the aorta edit mode 340. In addition, any ostia accepted from landmarks task 400 may be visible on all views and any accepted ostial segmentation from lumen task 700 may be visible on all views. In one embodiment, the option to "Accept Aorta" may remain inaccessible until either edit or create tools are used. In other words, the aorta task 300 may ensure that a user at least reviews images of an aorta before accepting it.

Figure 4A:
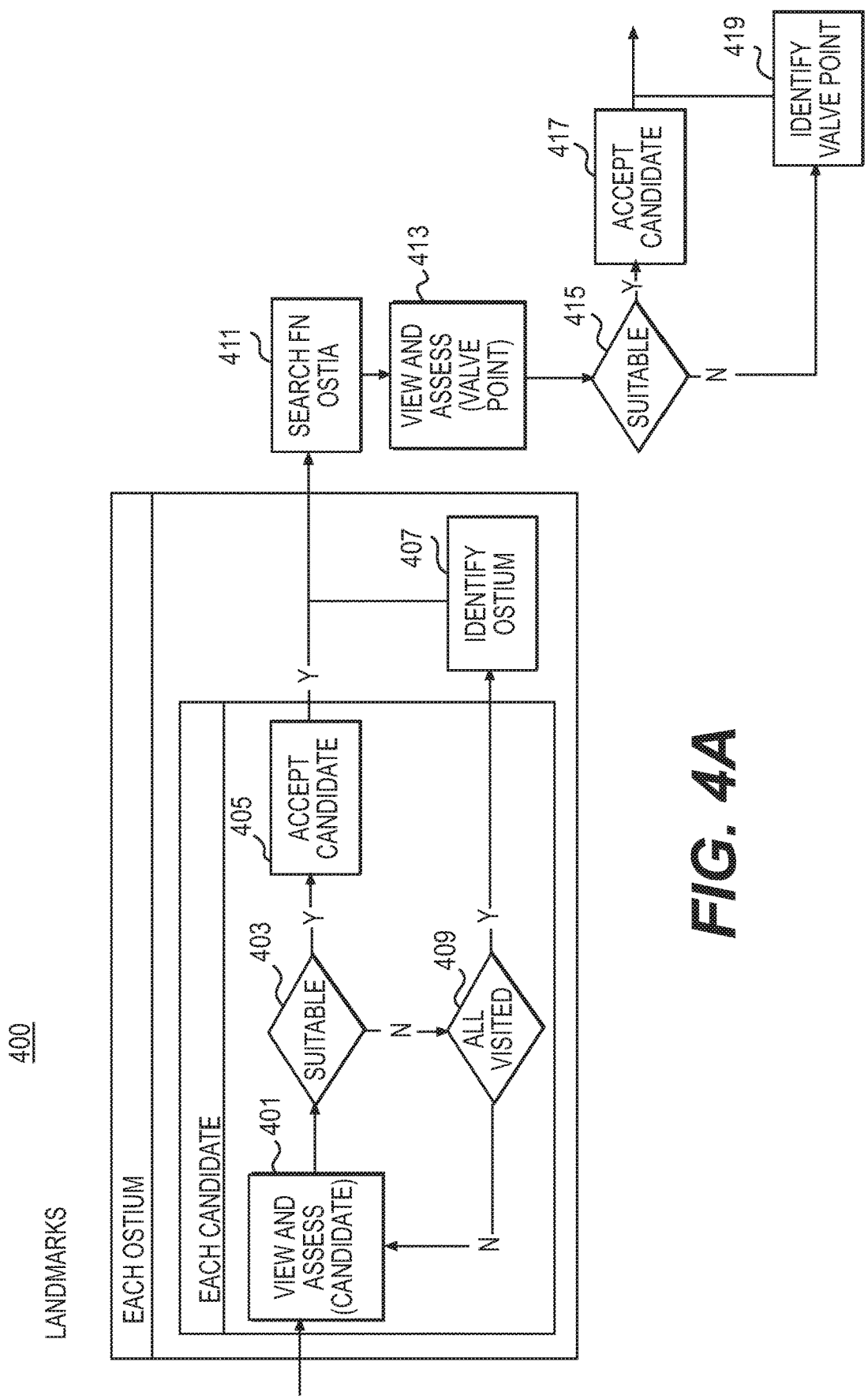
FIG. 4A is a block diagram of an exemplary landmarks task, according to an exemplary embodiment of the present disclosure.

FIG. 4A is a block diagram of an exemplary landmarks task 400, according to an exemplary embodiment of the present disclosure. Landmarks task 400 may be performed by server systems 106, based on information, images, and data received from physicians 102 and/or third party providers 104 over electronic network 100. In one embodiment, landmarks task 400 may be used to review and/or modify ostium points and the valve point. For example, landmarks task 400 may lead a user through identifying all correct ostia points, and then through identifying the correct location of the aorta valve point. The ostium points and valve point may serve to standardize origination of vessel centerlines and aorta trim planes, respectively. In one embodiment, the landmarks task 400 may be similar to the aorta task 300 in that a user may not proceed forward in the case unless at least ostium is identified.

In one embodiment, landmarks task 400 may have, essentially, only one mode (further described in FIG. 4B), although review and modification of ostium points and the valve point may occur sequentially. For example, landmarks task 400 may include viewing and assessing each candidate (i.e. each possible ostium) (step 401). Users may then be prompted to determine whether a candidate ostium is suitable (step 403). In one embodiment, a user may accept a candidate, thus verifying or "accepting" an ostium candidate (step 405). In one embodiment, accepting the ostium candidate may lead to actively identifying an ostium (step 407). In one embodiment where a user decides at step 403 that an ostium candidate is not suitable, a workflow may proceed to step 409 of determining whether all candidate ostium have been visited. If all candidates have been viewed and assessed, a user may be prompted to verify and actively identify the ostium (step 407). If not, the workflow may return to step 401, where a user is presented with another ostium candidate.

Once the ostia are identified, a workflow may proceed to step 411 of searching for ostia (e.g., imaging false-negative or "FN" ostia). For example, a user may be prompted to view and assess a candidate valve point (step 413). If the candidate valve point is deemed suitable (step 415), the candidate valve point may be designated as an accepted candidate and confirmed valve point (step 417). If the valve point is not deemed suitable at step 415, a user may be prompted to instead, identify a valve point (step 419).

Figure 4B:
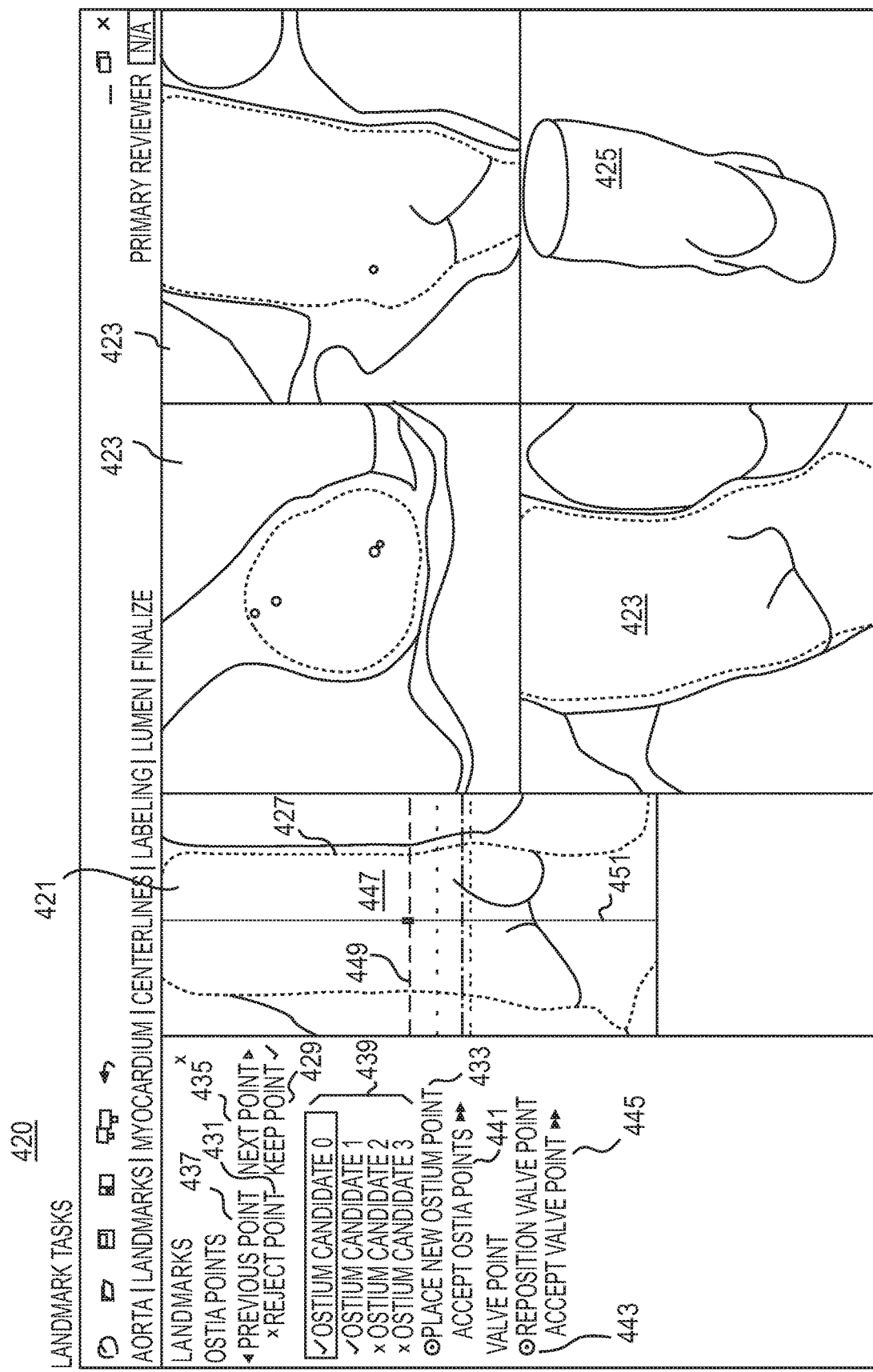
FIG. 4B is a display of landmarks mode, according to an exemplary embodiment of the present disclosure.

FIG. 4B is a display of landmarks mode 420, according to an exemplary embodiment of the present disclosure. As previously discussed, landmarks task 400 may not have separate modes. While review and modification of ostium points and the valve point may occur sequentially, both activities may occur using the same layout. In one embodiment, landmarks mode 420 may include one sCPR 421, three MPRs 423, and an ISO 425 in a VR. In one embodiment, the sCPR 421 may be located at the left of the screen, while the four other views may be in a 2×2 configuration, with the VR in the bottom right corner.

In one embodiment, the sCPR 421 may be constructed using an aorta centerline from the aorta task 300. In one embodiment, the sCPR 421 may be oriented such that the superior direction is towards the top of the screen. The sCPR 421 may be centered so that the top (i.e., first point) of the aorta centerline is located at the top border of the view. The sCPR 421 may be zoomed to a level of detail where the "radius" of the segmentation (with a buffer region) is shown in the view. The sCPR 421 may also be auto-window and/or leveled using aorta intensity to calculate the appropriate window and level.

In one embodiment, the MPRs 423 may be orthogonal to each other. Upon opening the task, the MPRs 423 may be aligned according to an aorta centerline. In one embodiment, the MPRs 423 may include a cross-sectional MPR located in the top left, a lateral MPR located in the top right, and an MPR orthogonal to the two other MPRs, located in the bottom left of a display. In one embodiment, the lateral MPRs may be oriented such that the superior direction is towards the top of the screen. The cross-sectional MPR's orientation may be initially set to synchronize with the longitudinal MPR. The MPRs may be centered around an aorta centerline point, and zoom may be the same across all MPR views. In one embodiment, the MPRs 423 may share the same window/level as the sCPR 421.

In one embodiment, the ISO 425 may be initially oriented such that the superior direction is towards the top of the screen, centered such that the 'center' of the aorta segmentation is at the center of the view, and zoomed such that the radius of the segmentation (with a buffer region) is shown in the view.

In one embodiment, landmarks task 400 may offer various paradigms for navigating through the aorta to identify landmarks. In a first embodiment, navigation may be constrained to lie along an aorta centerline. By using an Inspector Gadget 427 tool in the sCPR 421, a user may rotate and scroll along the aorta centerline. In a second embodiment, landmarks task 400 may offer full navigation capability, with easy navigation through an ostium candidate list. For example, the sCPR 421 may be rotated, where the Inspector Gadget 427 may synchronize navigation between a view of the sCPR 421 and views of respective MPRs 423. The MPRs 423 may have full rotation, scrolling, zooming, panning, re-centering, and windowing capabilities. In addition, when a candidate is selected from the ostium candidate list, the candidate may be re-centered on all three MPR 423 views. The VR view for ISO 425 may automatically re-center and rotate to show a currently selected ostium candidate as best as possible. In one case, the VR may have its own navigational controls, where the VR may be rotated, zoomed, and panned.

In one embodiment, ostium points may be accepted or rejected using a tool, for example, Keep Point 429. In one embodiment, exemplary button, Keep Point 429, may change a status of a selected ostium point to "Accepted." Exemplary button, Reject Point 431, may change a status of a selected ostium point to "Unaccepted." In both cases, a user interface and colors may update and a next candidate on a list may be selected.

In one embodiment, landmarks mode 420 may further include exemplary button, New Ostium Point 433. In one embodiment, New Ostium Point 433 may be used to add another candidate to the ostium list. In one instance, the new ostium may be added in an Accepted state. In a further instance, an inclusion zone may be displayed upon selection of New Ostium Point 433. For example, a contour of an inclusion zone may represent a space within boundaries of aorta segmentation where an ostium point may be placed.

Navigation may further include two tools: Next Point 435 and Previous Point 437. In one embodiment, these tools may help navigate to a next ostium candidate and previous ostium candidate, respectively, on an ostium list 439. Statuses (e.g. accepted or not accepted) may not be affected by using Next Point 435 and/or Previous Point 437. After all ostia have been reviewed and the ostium portion of landmarks task 400 is complete, exemplary button, Accept Ostia Points 441, may update the landmarks mode 420 to review of the valve point. In one embodiment of reviewing of the valve point, a user may only reposition the valve point, for example, using a tool, Reposition Valve Point 443. If the valve point that is displayed is incorrect, Reposition Valve Point 443 may move a valve point to a desired location. Like an ostia, an inclusion zone may be displayed to indicate where in the model a valve point may be placed.

When opening landmarks mode 420, a first portion of landmarks task 400 may be to review ostia points. In one embodiment, a first ostium may be automatically selected and centered in the views. A user may review the positioning of the first ostia to ensure that positioning is not too far off for centerline generation. If the positioning is acceptable, a user may opt to accept the ostium point (e.g., using Keep Pont 429). A user may choose to reject an ostium point if the positioning is not acceptable (e.g., using Reject Pont 431). After reviewing all ostia in the ostium list 439, a user may be prompted to review the aorta segmentation again for any missing ostia. If ostia are missing, the ostia may be added with New Ostium Point 433. Once all ostia have been reviewed and/or added, Accept Ostia Points 441 may be selected to move on to identifying the valve point. Again, the valve point may be automatically centered in the views. A user may review positioning of the valve point to ensure that a correct point is tagged. If the point is correct, exemplary button, Accept Valve Point 445, may be selected by a user. If the position is incorrect, a user may move the valve point after selecting Reposition Valve Point 443. After repositioning the valve point, a user may subsequently select Accept Valve Pont 445.

In one embodiment, Accept Ostia Points 441 may be selected to move from ostia review to valve point review. To move onto the next task, myocardium task 500, a user may select the last selection of landmarks mode 420, Accept Valve Pont 445. In one embodiment, both the ostia and valve point may serve as guiding points for algorithms further along in the workflow. The ostia may serve as starting points for vessel centerlines. Thus, if an unaccepted ostium is accepted by a user, a centerlines algorithm may run using merely accepted ostia and possibly, newly placed ostia added by a user. Similarly, if previously accepted ostia are rejected, centerlines corresponding to those ostia may be cleared. The valve point may serve as a landmark for an aorta centerline. The aorta centerline may be used later in the workflow. For example, the aorta centerline may be used during modeling to accurately trim an aorta inlet at a valve plane. Then, upon acceptance of the valve point, an aorta centerline may be recomputed.

In one embodiment, a series of settings may be the default, upon a user returning to landmarks task 400. For example, the first ostium point of ostium list 439 may be selected upon a user re-opening landmarks task 400. In one embodiment, Accept Ostia Points 441 may remain inaccessible until an ostium point is added to the list or until a status is changed. After selecting Accept Ostia Points 441, a user may go to the valve point section and be prompted to re-accept the valve point to move on to another task.

In one embodiment, the landmarks mode 420 may have a progress bar overlaying the task name. The progress bar may only be visible during the landmarks task 400. In one embodiment, progress for the landmarks task 400 may first be divided by "sub-tasks" in landmarks task 400. For example, identification of ostia may count towards 75% of the bar and deification of the valve point may count towards 25%. Within the ostium portion, acceptance or rejection of each ostium may count towards an equal portion of the 75%. Thus, as a user accepts or rejects each ostium, the bar may progressively fill to 75%, in increments based on the total ostia available for processing. For example, the increments may be equal in size, based on the total available ostia. The bar may also fill just as a visual guideline, where the increment size may not directly correspond to and acceptance or rejection of each ostium. In one embodiment, if an ostium point is added, the percentage of each ostium may be shifted so that a visual portion of the progress bar is equal, but will add to the total length of the progress bar (since the ostium is added in an accepted state). After a user accepts all ostia, the bar may be at 75% completion. After accepting the valve point, the bar may reach 100% completion.

In one embodiment, the Inspector Gadget 427 may be displayed in the landmarks mode 420 on the sCPR 421. In one embodiment, a dot 447 may indicate rotation of the sCPR 421 and serve as indication to a user that rotation of the MPRs 423 may be controlled by rotation on the sCPR 421. In addition, positioning of line 449 along a centerline may indicate a centering position of the views of the MPRs 423. Since the landmarks mode 420 may have at least two different methods of navigation, synchronization of the views with the centering point may only be represented accurately when navigation using the Inspector Gadget 427 is used. If further navigation is used on the MPRs 423, the MPRs 423 may be oriented such that Inspector Gadget 427 may not be displaying the centering position.

In one embodiment, the sCPR 421 may include a display of a relative position of a selected ostium point or valve point. For example, a solid line 451 across the sCPR 421 may indicate a projected location along the centerline of the point. In one embodiment, line 451 may serve as a reference so that the Inspector Gadget 427 may be used to locate a position of the ostium point or valve point accurately. Accurately locating the ostium point and/or valve point may permit the MPRs 423 to be displayed accurately.

Figure 5A:
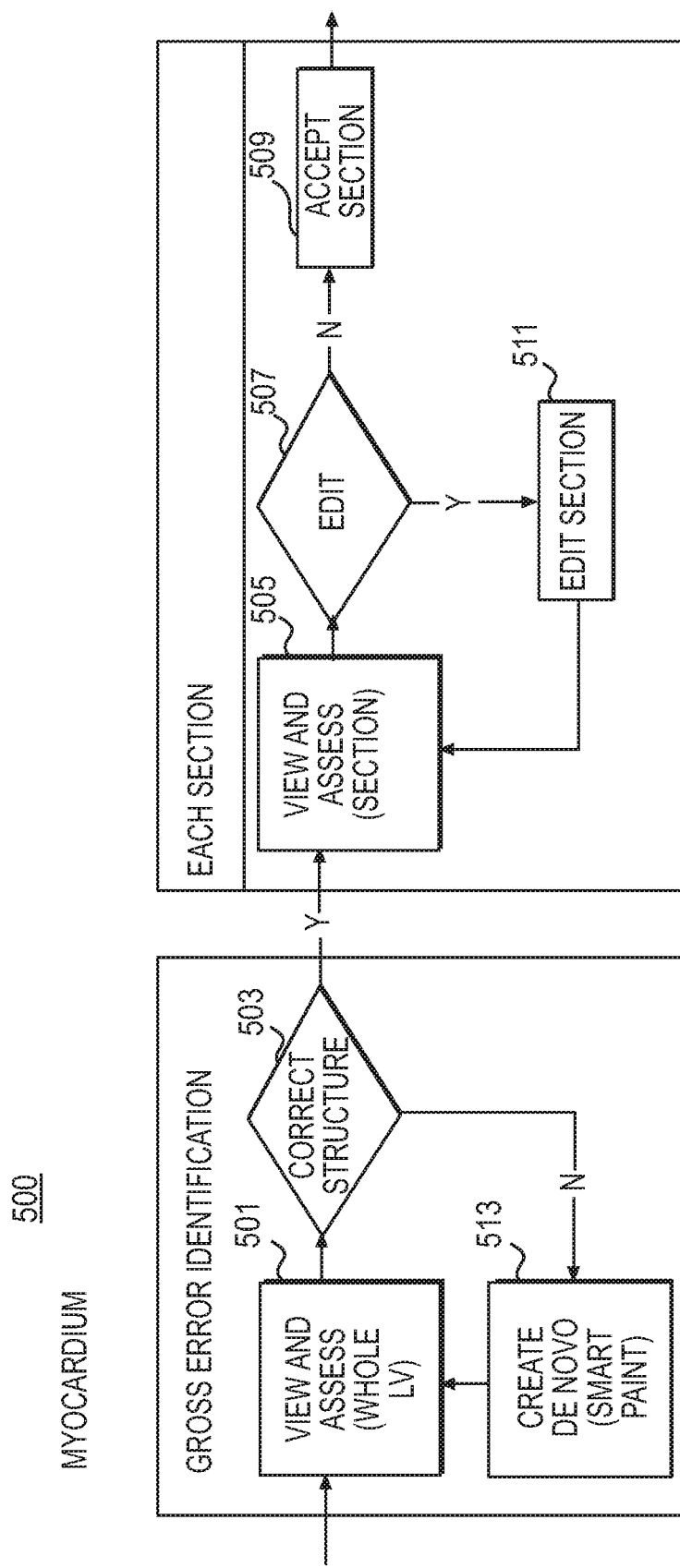
FIG. 5A is a block diagram of an exemplary myocardium task, according to an exemplary embodiment of the present disclosure.

FIG. 5A is a block diagram of an exemplary myocardium task 500, according to an exemplary embodiment of the present disclosure. Myocardium task 500 may be performed by server systems 106, based on information, images, and data received from physicians 102 and/or third party providers 104 over electronic network 100. In one embodiment, myocardium task 500 may be used to segment the left ventricle. For example, the left ventricular mass may be used for a computational fluid dynamics (CFD) solution, meaning a CFD solution may be calculated from the volume of a left ventricle segmentation. In one embodiment, a series of images or annotations used for the left ventricle segmentation may be different from a series used for a lumen. In one analysis, the quality of each series may be calculated for both lumen processing and left ventricle processing. Since a diastolic phase may be vastly preferred for segmenting the left ventricle, the diastolic phase may be prioritized in almost all cases for left ventricle segmentation. In one embodiment, a user may not proceed forward without an accepted left ventricle segmentation with a mass in an acceptable range, similar to previous tasks (e.g., red flags task 200, aorta task 300, and landmarks task 400).

To aid in segmenting the left ventricle, myocardium task 500 may include two components: gross error identification and closer inspection of each section. In one embodiment, myocardium task 500 may be analogous to aorta task 300, where gross structure may be evaluated first, then finer analysis may be performed for each section. In one embodiment, myocardium task 500 may begin with step 501 of gross error identification, where a user may be prompted to view and assess an left ventricle, basically in its entirety. The user may be prompted to determine whether the gross structure is correct (step 503). If a user selects that the structure is generally correct, the user may then be presented with more detailed analysis, including step 505 for viewing and assessing various sections of the left ventricle. In one embodiment, a user may choose to edit the section (step 507). Subsequently, a user may either accept the section (step 509) or further edit the section (step 511). In one embodiment where a user may determine after viewing the gross structure of the left ventricle (step 501) that the structure is faulty, a user may select to create de novo a new model of the left ventricle (step 513). In one embodiment, step 513 may be completed using a tool, for example, Smart Paint.

In one embodiment, myocardium task 500 may provide tools, views, and navigation capabilities to assist in review and modification of myocardium segmentation. Specifically, the myocardium task 500 may be comprised of three modes: myocardium inspect mode 520, myocardium edit mode 540, and myocardium create mode 560. In one embodiment, each mode may include different tools and views for reviewing, editing, and creating the myocardium segmentation.

Figure 5B:
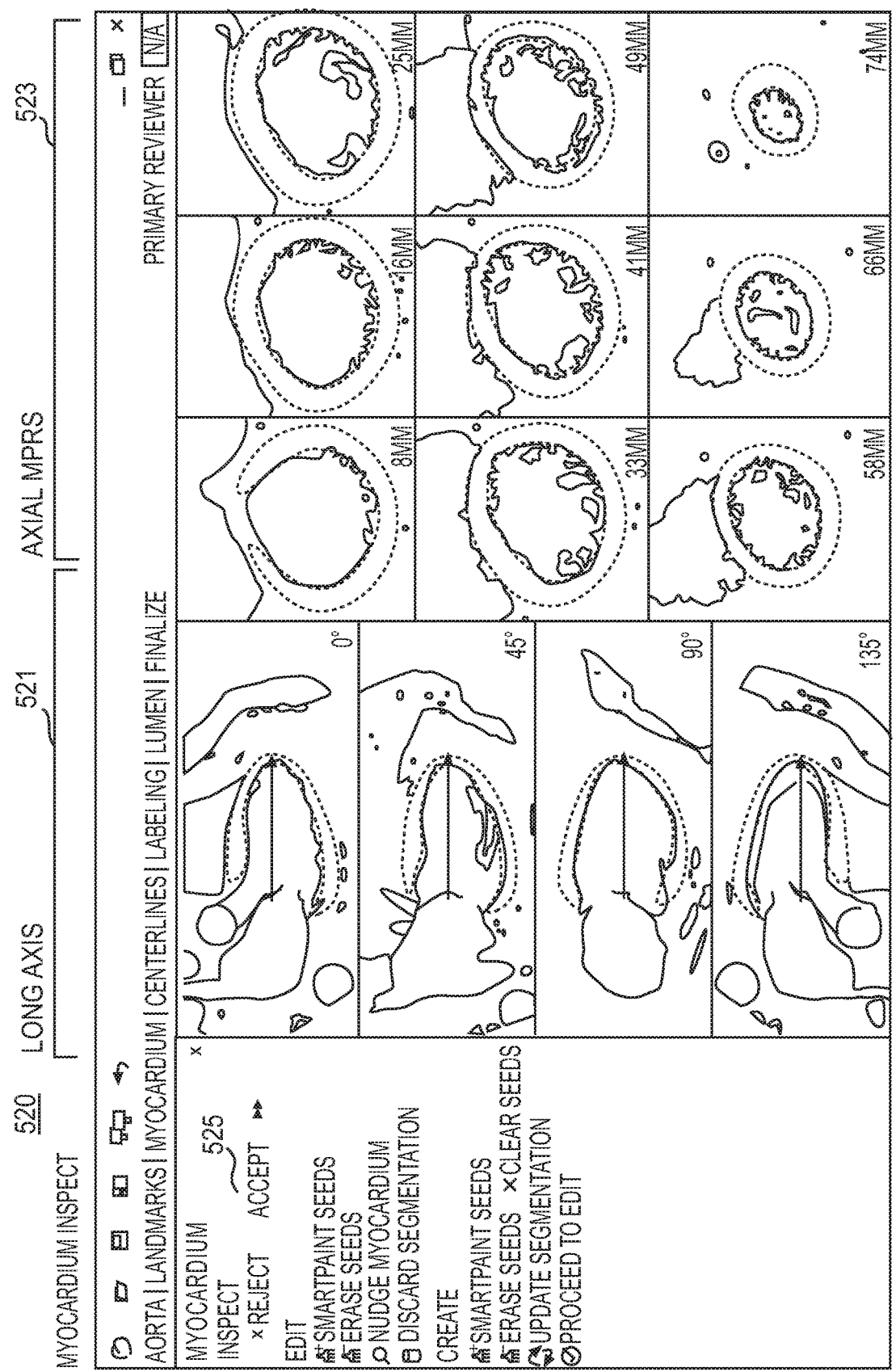
FIG. 5B is a display of myocardium inspect mode, according to an exemplary embodiment of the present disclosure.

FIG. 5B is a display of myocardium inspect mode 520, according to an exemplary embodiment of the present disclosure. In one embodiment, the myocardium inspect mode 520 may permit a user to quickly determine whether gross structure and segmentation of a myocardium generated by an automatic algorithms is sufficient to proceed, or requires modification. In one embodiment, myocardium inspect mode 520 may include four long axis MPRs 521 and nine axial MPRs 523. In one embodiment, the long axis MPRs 521 may occupy a left side of a screen, while axial MPRs 523 may be arranged on the right. The views may be constructed from a long axis of the myocardium segmentation, which may be determined by apical and basal points.

In one embodiment, long axis MPRs 521 may be constructed using the myocardium long axis, by taking slices at 0°, 45°, 90°, and 135°. The views may be oriented such that the apex of the heart is towards the right side of the screen, with the base towards the left of the screen. Segmentation may be centered in the views, such that the long axis is along the horizontal axis of a view. The views may be zoomed such that a segmentation's closest point to a window boundary may be some buffer away from the boundary.

In one embodiment, the axial MPRs 523 may be constructed by taking nine cross-sectional slices along the long axis of the myocardium. The slices may be equally spaced and span the entirety of the long axis. In one embodiment, apical and basal slices may be placed a small distance from the apex and base so that the top and bottom slices do not show only specks of segmentation. In one embodiment, the MPRs 521 and 523 may be oriented such that the 0° direction is towards the top of the view. The MPRs 521 and 523 may be centered such that the long axis is at the center of the view. The views may all share the same zoom, where the zoom of all MPRs 521 and 523 may be based on the zoom of the slice with the largest segmentation. In one embodiment, that slice with the largest segmentation may be zoomed such that the segmentation's closest point to the window boundary is some buffer away from the boundary.

In one embodiment, navigation may be disabled for views in the myocardium inspect mode 520. The initial set-up of the views may support a quick decision regarding correctness of the segmentation, so navigation may be reserved for other modes of myocardium task 500. Myocardium inspect mode 520 may just be intended for gross error identification, so in one embodiment, myocardium inspect mode 520 may include only tools to accept the segmentation (e.g., a tool, Accept 525) or reject the segmentation (e.g., a tool, Reject 527). If Accept 525 is selected, the myocardium task 500 may be complete and centerlines task 600 may commence. If Reject 527 is selected, the myocardium inspect mode 520 may still be seen as complete, but myocardium edit mode 540 may be enabled. With myocardium edit mode 540, a user may correct the segmentation that caused him to reject the segmentation during the myocardium inspect mode 520.

Figure 5C:
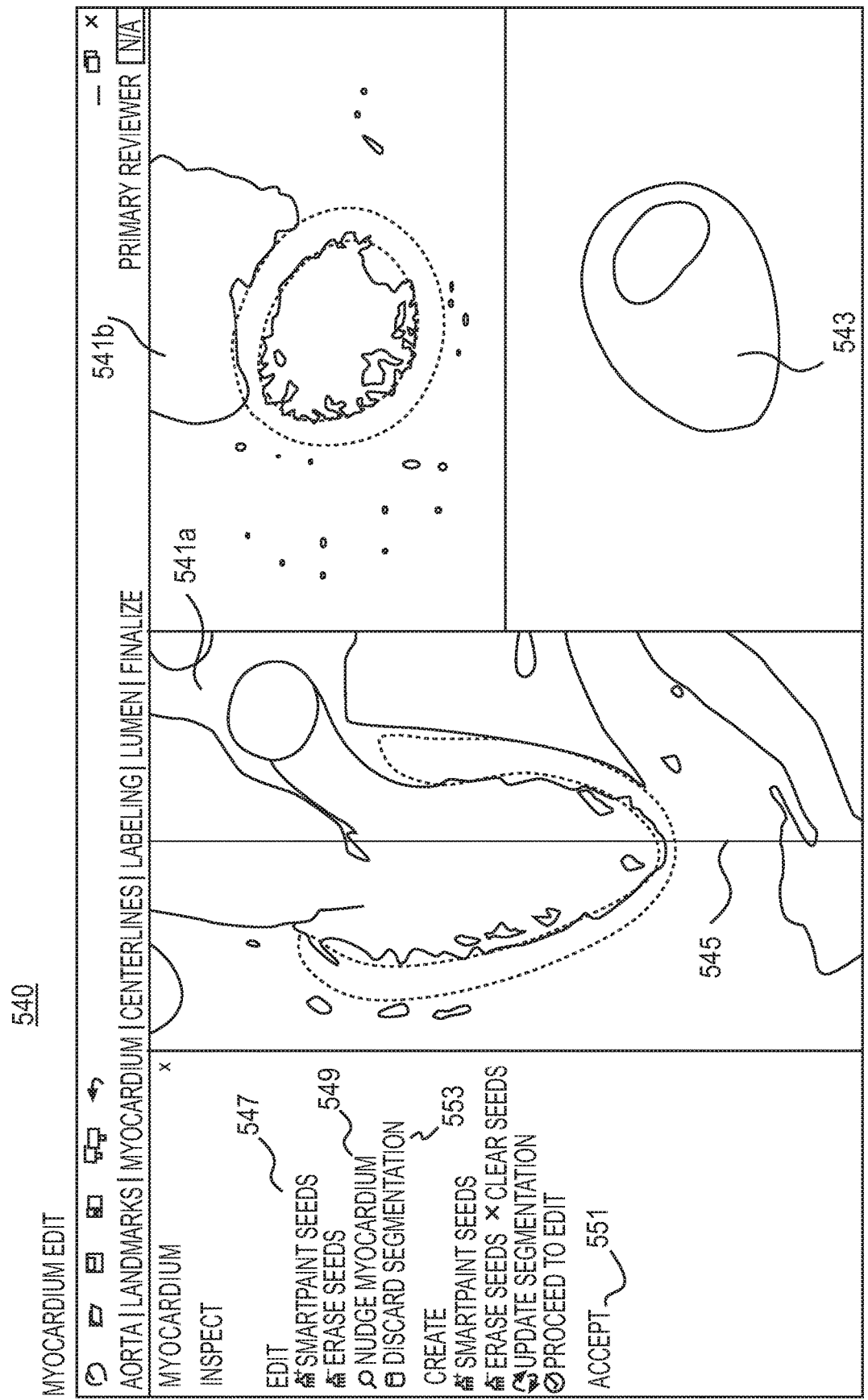
FIG. 5C is a display of myocardium edit mode, according to an exemplary embodiment of the present disclosure.

FIG. 5C is a display of myocardium edit mode 540, according to an exemplary embodiment of the present disclosure. In one embodiment, the myocardium edit mode 540 may permit quick and confident edits to myocardium segmentation so that accurate and reproducible myocardium segmentation may be obtained. In one embodiment, the myocardium edit mode 540 may include two MPRs 541a and 541b and one ISO/VR 543. In one embodiment, MPR 541a may be a long axis MPR that occupies the left half of the myocardium edit mode 540. MPR 541b may be an axial view MPR that occupies the top right half of the display myocardium edit mode 540. The ISO/VR 543 may occupy the bottom right half of the view.

In one embodiment, the log axis MPR 541a may be oriented to display the apex of the heart at the bottom of the view and the base at the top of the view. In one embodiment, both MPR 541a and 541b may have their zoom level based on the size of contours in the view. The long axis MPR 541a may zoom the view so that the nearest segmentation contour has some buffer away from the border of the view. The axial MPR 541b may have a zoom such that the largest contour also has some buffer away from the border of the view.

In one embodiment, navigation in the myocardium edit mode 540 may be based primarily on Inspector Gadget 545. In one embodiment, the Inspector Gadget 545 may permit a user to probe a particular axial slice in the myocardium. The Inspector Gadget 545 may further permit a user to rotate the long axis MPR 541a to display the long axis view. The ISO/VR 543 may also be rotated to inspect for holes or bumps.

In one embodiment, Smart Paint 547 and Nudge 549 may be available tools in myocardium edit mode 540. In one embodiment, these tools may have functionalities specific to the myocardium edit mode 540. For example, segmentation may automatically update after placing inside or outside seeds. Due to the nature of the myocardium task 500, myocardium task 500 may include an "inner" contour and an "outer" contour. The inner and outer contours may be respected when a user employs Smart Paint 547. Smart Paint 547 in myocardium edit mode 540 may be analogous to Smart Paint 349 in the aorta edit mode 340. In one embodiment, the same code may be used for Smart paint 349 and Smart Paint 547.

In one embodiment, the tool for Nudge 549 may also have functionality particular to the myocardium task 500. For example, due to the inner and outer contour, a user may create disconnections in the segmentation by using Nudge 549. For example, Nudge 549 may be used to push contours in whatever direction a user may move his pointer. In one embodiment, a contour may be sensitive to any pointer movement or selection when using Nudge 549. For example, pointer movement may shift the position of the contour, and a selection may be read at myocardium edit mode 540 as punching a hole through the segmentation. In such cases, a user may use caution regarding where to place a start point of the nudge movement, so as to not make unexpected or unintentional alterations to contours or segmentation.

In one embodiment, myocardium edit mode 540 may further include the ability to accept and/or reject segmentation. For example, when all edits have been completed and a user deems segmentation to be correct, the user may select a tool (e.g., Accept 551) to move onto centerline task 600. If myocardium edit mode 540 may not be used to complete segmentation in a reasonable amount of time, a user may have the option to create a new segmentation. To provide a user with these options, myocardium edit mode 540 may include a tool, e.g., Discard Segmentation 553, which may automatically bring a user to myocardium create mode 560.

Figure 5D:
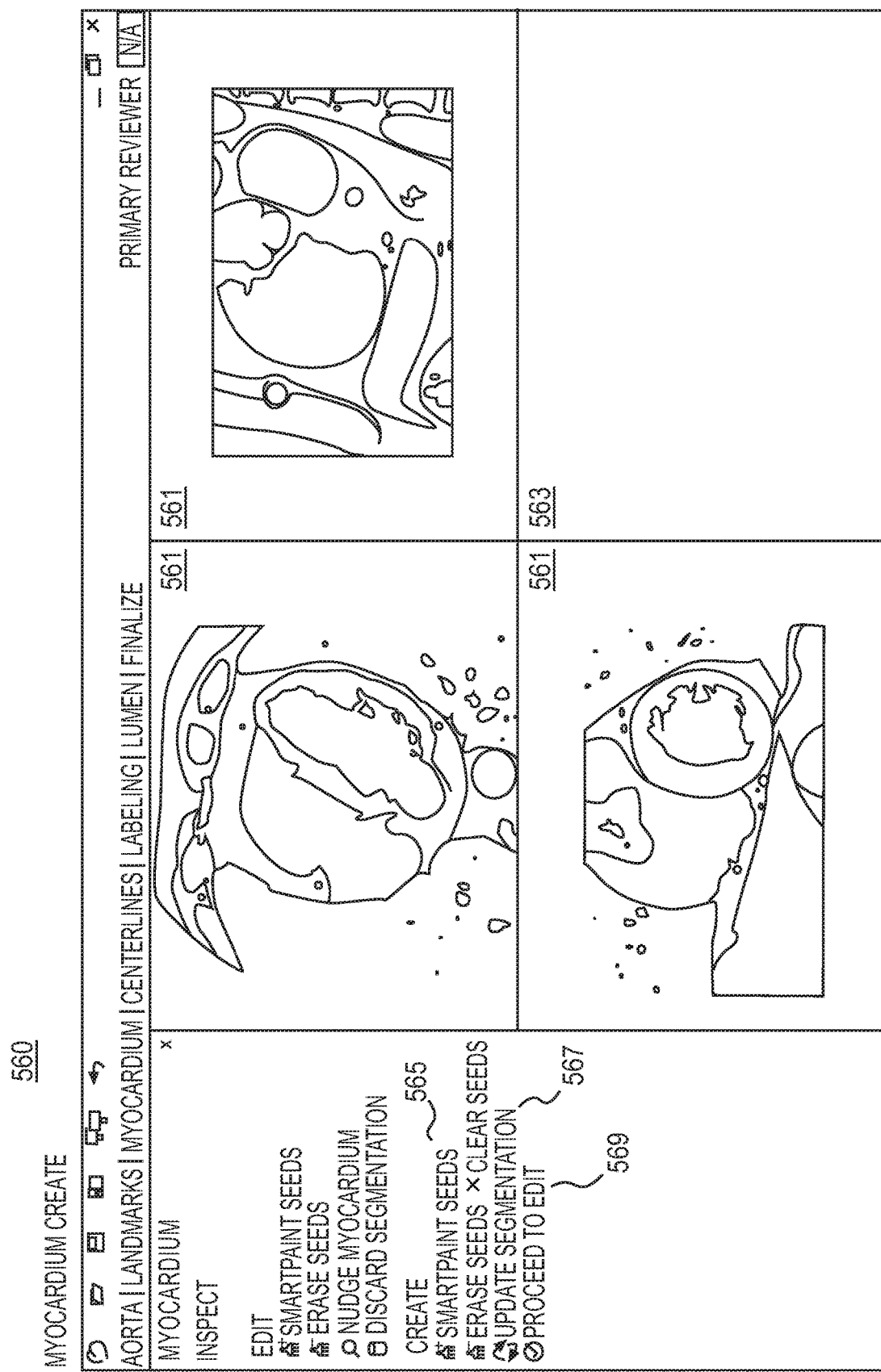
FIG. 5D is a display of myocardium create mode, according to an exemplary embodiment of the present disclosure.

FIG. 5D is a display of myocardium create mode 560, according to an exemplary embodiment of the present disclosure. In one embodiment, myocardium create mode 560 may provide views, tools, and navigation for a user to create a myocardium segmentation. Myocardium create mode 560 may be used if a pipeline algorithm produces a segmentation that misidentifies the myocardium, produces a large number of errors, produces errors cumbersome to resolve in myocardium edit mode 540, or a combination thereof.

In one embodiment, a standard layout for myocardium create mode 560 may include three MPRs 561 and one ISO/VR 563. In one embodiment, the three MPRs 561 may show the transverse, coronal, and sagittal planes. The MPRs 561 may be centered at the image volume center and initially zoomed to a degree such that the image volume fills at least one of the views. In one embodiment, the MPRs 561 may all have the same window and/or level, set to an automatic preset. In a further embodiment, the three MPRs 51 may share a centering point, zoom, and/or window level. Rotation may be synchronized between the three MPRs such that the plans being displayed at any given time may consistently remain orthogonal.

In one embodiment, the ISO/VR 563 may be initially blank when myocardium create mode 560 opens. The ISO/VR 563 may populate as myocardium segmentation is generated. The ISO/VR may be oriented such that the superior direction is towards the top of the screen and centered such that the "center" of the myocardium segmentation is at the center of the view. The ISO/VR 563 may be zoomed such that the radius of the segmentation (plus a buffer portion) is shown in the view.

In one embodiment, navigation may be available in myocardium create mode 560. For example, users my rotate, pan, re-center, zoom, and adjust window and/or levels on any of the MPRs 561. In one embodiment, myocardium create mode 560 may include a tool, Smart Paint 565. For instance, updating for the segmentation may occur when a user selects a tool, e.g., Update Segmentation 567. In one embodiment, the segmentation may be recalculated based only on the seeds from Smart Paint 565, meaning the initial segmentation may be discarded. In one embodiment, this update may take longer than Smart Paint 365 from aorta create mode 360 because of the recalculating. In one embodiment, the Smart Paint 565 may only work on MPRs 561. Myocardium create mode 560 may further include a tool for mode switching, e.g., Proceed to Edit 569. In one embodiment, a user may return to myocardium edit mode 540 to review segmentation, where the myocardium long axis may be used to review the myocardium segmentation.

In summary, in one embodiment, myocardium task 500 may begin at myocardium inspect mode 520. If all the displayed contours of the ventricle look accurate to a user, the user may immediately select to accept the model and move on to centerlines task 600. If the user is unsure or if he wishes to modify the segmentation, the user may select a tool to reject the segmentation or select to go to myocardium edit mode 540. In myocardium edit mode 540, a user may navigate to relevant slices (e.g., using Inspector Gadget 545) in order to make changes. In one embodiment, a user may employ Smart Paint 547 to edit the segmentation. When a user completes his edits from Smart Paint 547, a user may use Nudge 549 for fine adjustments. If the edit tools Smart Paint 547 and Nudge 549 are insufficient to successfully finish the segmentation, a user may elect to reject the segmentation and enter myocardium create mode 560.

In myocardium create mode 560, a user may start with standard views of the myocardium, oriented along sagittal, coronal, and transverse planes. The views may be oriented as best as possible so that one view displays the axial plane along the perceived myocardium long axis. The other two views may automatically align to display two long axis views. Users may use a tool (e.g., Smart Paint 565) on two long axis views to define a range of the myocardium. In one embodiment, myocardium create mode 560 may further provide guidance to users to take extra caution to include outside seeds in the left ventricular pool and to exclude visible papillary muscle. A user may add seeds to another view so that both views have inside and outside seeds, defining a region of interest (ROI) within which to operate. Segmentation may be updated (e.g. using Update Segmentation 567) when a user feels that he has finished editing. Selecting Update Segmentation 567 may prompt myocardium create mode 560 to calculate the segmentation. After segmentation is generated, a user may review the result and verify that no gross errors are present. If errors are noted, the errors may be corrected immediately (e.g., using Smart Paint 565). If no errors are noted, a user may return to myocardium edit mode 540 (e.g., by selecting Proceed to Edit 569). In myocardium edit mode 540, a user may again review the segmentation using the views and tools available from myocardium edit mode 540. In one embodiment, a shape model may automatically be used. In a further embodiment, a toggle option may be available to toggle between a shape model output and a raw smart paint output.

In terms of switching modes, the myocardium task 500 may include myocardium inspect mode 520, myocardium edit mode 540, and myocardium create mode 560. A user may move sequentially from myocardium inspect mode 520 to myocardium edit mode 540 and between myocardium edit mode 540 and myocardium create mode 560. Additionally, a user may advance to a next task (e.g., centerlines task 600) from either myocardium inspect mode 520 or myocardium edit mode 540.

In one embodiment for myocardium inspect mode 520, a user may select to reject a segmentation and move to myocardium edit mode 540 if the segmentation appears wrong. In myocardium edit mode 540, a user may select to reject editing and completely discard the segmentation if editing may not create sufficient modification to make an acceptable segmentation. After discarding the segmentation, a user may proceed to myocardium create mode 560. As previously discussed, after segmentation is completed in the myocardium create mode 560, a user may elect to return to the myocardium edit mode 540 and review the segmentation. In both the myocardium inspect mode 520 and myocardium edit mode 540, a user may select to accept the segmentation and move on to the centerlines task 600 if the myocardium segmentation is correct. In one embodiment, the myocardium create mode 560 may not offer the option to directly accept segmentation.

In one embodiment, several background calculations may occur regarding the myocardium segmentation. First, the myocardium long axis may be recalculated if a user returns to the myocardium edit mode 540 following the myocardium create mode 560. In addition, myocardium task 500 may include suggested trimming locations in centerlines task 600, that are based, at least in part, on detection of myocardial bridging. In one embodiment, the boundary of the myocardium may be used to determine when a vessel dips into the myocardium.

In one embodiment, if a user returns to the myocardium task 500, myocardium edit mode 540 may be activated as the default screen. The option to accept (e.g., using Accept 551) may be inaccessible until edit tools or create tools are used on the segmentation. In other words, a user who returns to the myocardium task 500 may make some modification before segmentation may be accepted.

In one embodiment, a progress bar may overlap with a myocardium tab when myocardium task 500 is the active task. This progress bar may track completion of the myocardium task 500 and progress to 100% if the myocardium is accepted. For the myocardium inspect mode 520, positioning of the long axis and axial MPRs 523 may be displayed on the long axis MPRs 521. As a user hovers over an axial MPR 523, the location of the slice may be displayed on the long axis MPR 521.

Figure 6A:
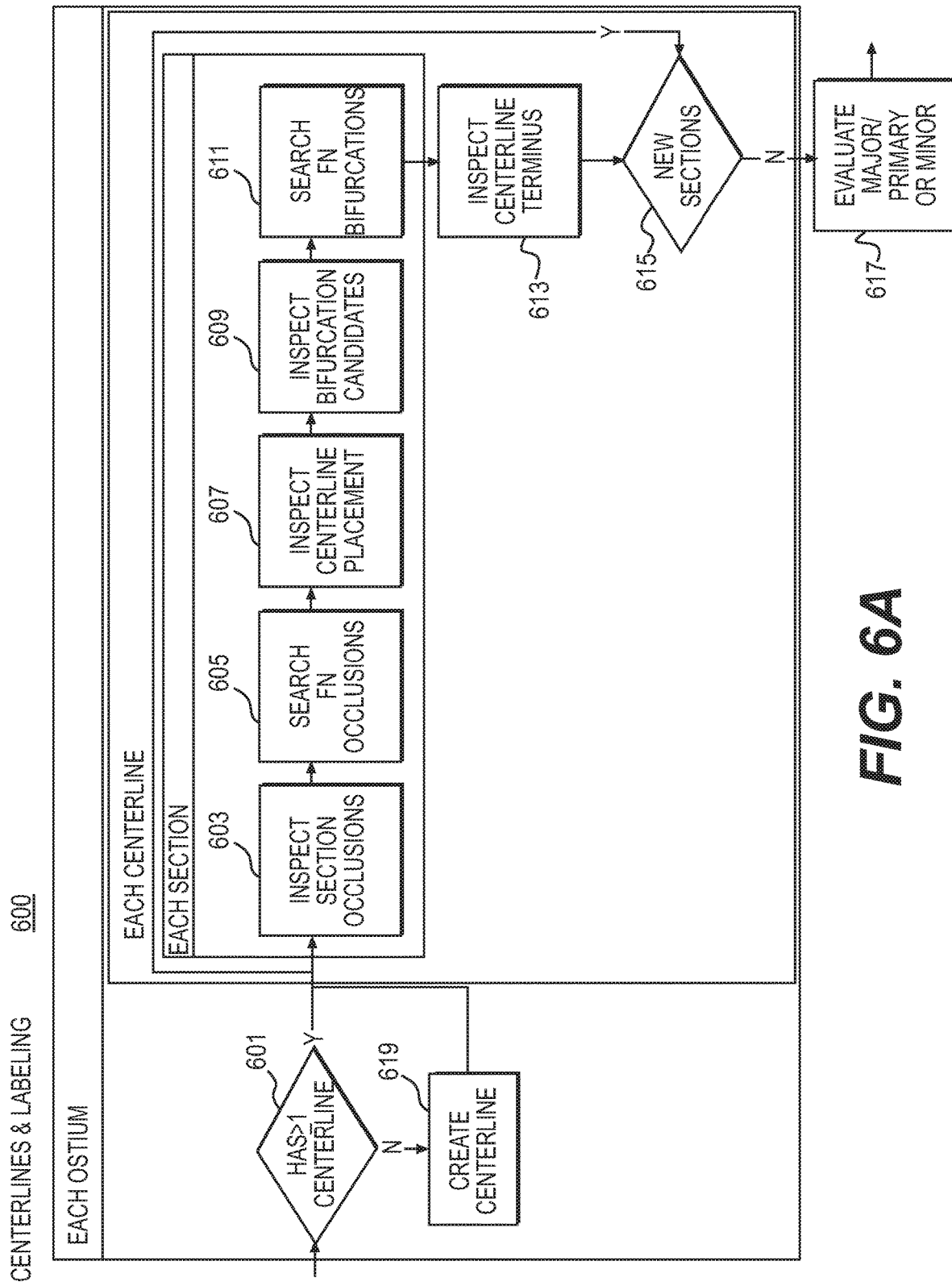
FIG. 6A is a block diagram of an exemplary centerlines task, according to an exemplary embodiment of the present disclosure.

FIG. 6A is a block diagram of an exemplary centerlines task 600, according to an exemplary embodiment of the present disclosure. Centerlines task 600 may be performed by server systems 106, based on information, images, and data received from physicians 102 and/or third party providers 104 over electronic network 100. In one embodiment, centerlines task 600 may be used to review a centerline tree, for example, in predefined centerline lengths (e.g., sections) in a predefined order. In one embodiment, a user may start with the right coronary artery (RCA) and review sections in order from proximal to distal parts of a main vessel. The main vessel may be determined based on automatic calculations and the determination may be updated in the next task (e.g., centerlines labeling task 640). After section review on the main vessel, a user may be provided with options to review the most proximal branch on the main vessel and all branches from the main vessel, moving from proximal to distal parts of the vessel. Following the RCA tree review, a user may review the LAD tree, then the left circumflex artery (LCX) tree. In on embodiment, the user may not proceed to the next task without identifying and accepting at least one centerline from each ostium point.

Figure 7A:
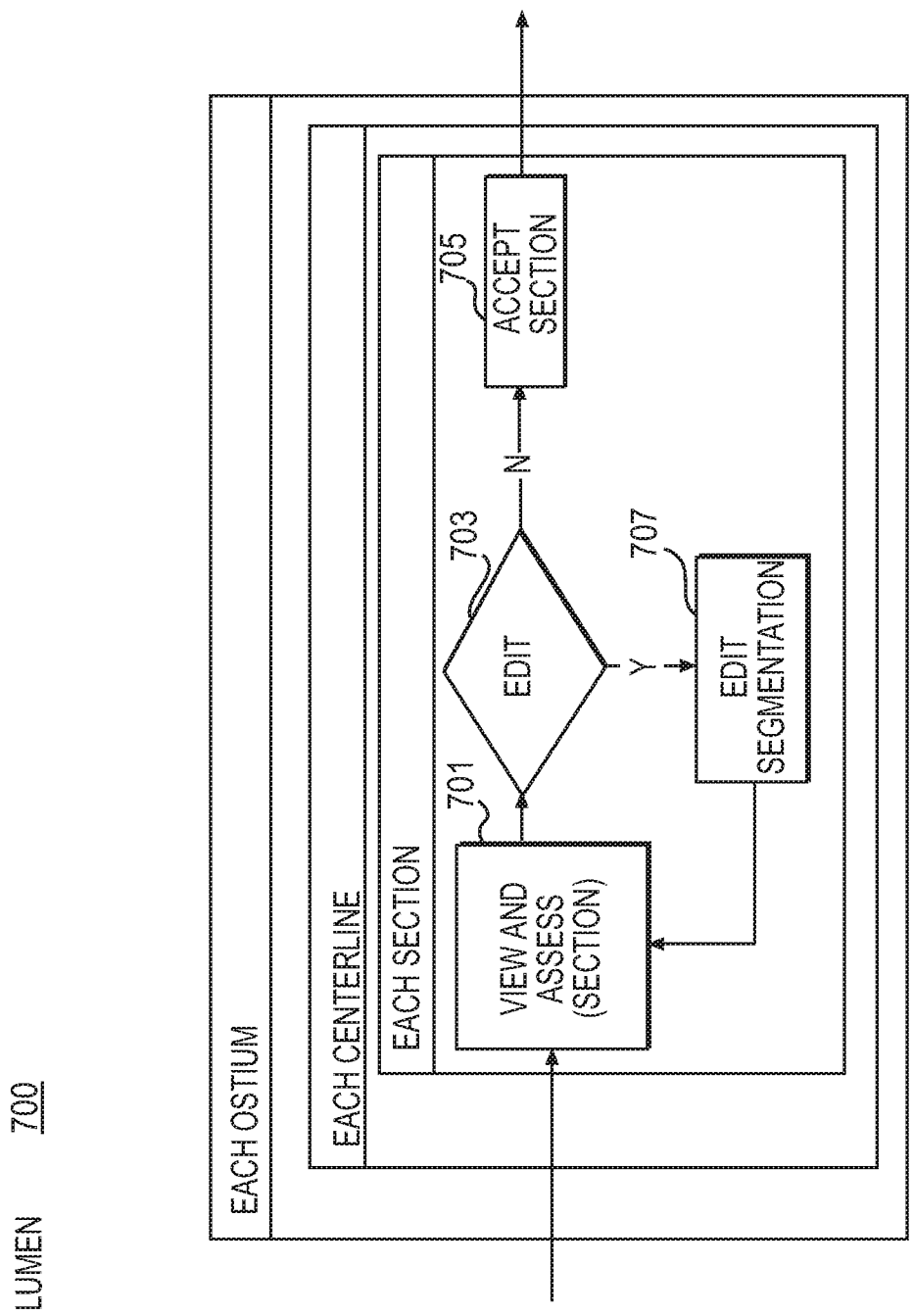
FIG. 7A is a block diagram of an exemplary lumen task, according to an exemplary embodiment of the present disclosure.

In other words, centerlines task 600 may be used to generate a centerline tree usable for lumen task 700 (e.g., shown in FIG. 7A). To do so, the centerlines task 600 may include automatic navigation, sections, tools, and a directed and tracked workflow to permit a user to quickly inspect, add to, delete from, and edit the centerline tree. In one embodiment, the centerlines task 600 and lumen task 700 may be designed for identifying correct vessels, as well as identifying correct topology. Thus, tools are provided to add to the centerline tree, delete from the centerline tree, and to edit the position of the centerlines.

In one embodiment, centerlines task 600 and lumen task 700 may include workflows organized into sections. For example, centerlines task 600 and lumen task 700 may employ sections as a means of breaking up the data and segmentation into manageable portions. Sections may refer to consecutive lengths of centerline along a single centerline path. For example, sections may begin at the first point on the centerline path, and proceed in the proximal-to-distal direction. In some cases, section length may be constant across all centerline paths, except possibly at terminal sections of each path. At the terminal sections, if the section is too small, the section may be combined into the previous section. Centerline sections may also be dependent on the order. If a main vessel definition is changed, sections may be recalculated and may be updated from the previous definition and ordering. Thus, a single centerline may have several sections defined along its length. Main vessels, especially, may include more sections defined along its length due to the ordering. For this reason, the main vessel may be reviewed first.

In one embodiment, sections may also represent a currently available piece of a segmentation that a user may be validating or modifying. For example, tools in both centerlines task 600 and lumen task 700 may pertain to local sections. For instance, the tools may be unavailable for an entire vessel tree or segmentation. This way, a user may have a consistent experience with tools, and not have to worry about how the use of the tool will affect the segmentation in unexpected ways.

In one embodiment, sections also have a clear indication of its status. Section status serves as a method for keeping track of work that has been done and for keeping track of work that has to be redone. For centerlines task 600, sections may be either "unaccepted" or "accepted." In one example, all sections may start as "unaccepted," while awaiting review by a user. If no changes are needed for the length of centerline, a user may select "Accept" to approve or validate the section. Tool use in an "accepted" section may change the status of the section back to "unaccepted," where the section may be re-accepted for validation. For lumen task 700, sections may be "un-reviewed," "reviewed," or "accepted." Sections may start as "un-reviewed." After a user reviews the section, the status may change to "reviewed." When the section and all adjacent sections are reviewed, the section status may be updated to "accepted." Tools may affect un-reviewed or reviewed sections, but accepted sections may remain the same. For both centerlines task 600 and lumen task 700, the user may be prompted to accept all sections prior to navigating or advancing to a next task.

In one embodiment, sections may be ordered according to vessel hierarchy, and by distance from the ostium point. First, sections may be ordered from proximal to distal along the main vessel centerline. After the main vessel, the most proximal branch may be next in order. Branches may be ordered according to proximity to the ostium.

Sections may also be recomputed through several different methods. For example, in centerlines task 600, any tool that changes the length of the centerline may prompt a re-computation of sections. These tools may include: a reposition tool, a trim tool, an extend tool, and a spline tool. In lumen task 700, sections may be recomputed based on changes in the centerline tree or changes in labeling. If a bifurcation is added, lumen sections may be computed on sections dependent on a recomputed section. The lumen segmentation may also be recomputed. In some cases, a section containing a newly added bifurcation may be updated to a status of "Un-reviewed." If the length of a section changes through use of the reposition tool, lumen sections may be recomputed for a current centerline path. In such a case, lumen segmentation may not be recomputed and the status may be changed to the lowest previous section status. If the centerline is trimmed, the terminal section may be cropped. In some embodiments, trimming of the centerline may not prompt re-computation of the segmentation, but status of a segmentation may be changed to "un-reviewed." If labeling is changed, order of vessel validation may be affected. Where ordering changes, sections may be recomputed on the affected vessels. Status may also be updated to the lowest previous section status. In situations where a user may edit a lumen to exclude an accepted centerline, a corresponding lumen section may cease to have an option to "accept" the section. To do so, the user may navigate back to the centerlines task, correct the centerline, and reaccept the centerline section.

In one embodiment, centerlines task 600 may include reviewing each ostium by reviewing each centerline (e.g., in sections). For example, centerlines task 600 may start with determining whether an ostium has at least one centerline (step 601). If so, a user may move on to inspect each section (e.g., using steps 603-611). For example, inspecting each section may include first, inspecting section occlusions (step 603). For example, a user may search imaging false-negative occlusions (e.g., "FN occlusions") (step 605) and inspect centerline placement (step 607). Afterwards, a user may inspect bifurcation candidates (step 609) and search imaging false-negative bifurcations (e.g., "FN bifurcations") (step 611). In one embodiment, a user may inspect a centerline terminus (step 613) after inspecting a section. If the terminus is identified as a new section (step 615), section analysis (e.g., using steps 603-611) may begin again for the new section. If a new section is not identified at step 615, a user may evaluate whether the terminus is major/primary or minor (step 617). In one embodiment, if no ostium is detected at step 601, a user may opt to create a centerline (step 619).

Figure 6B:
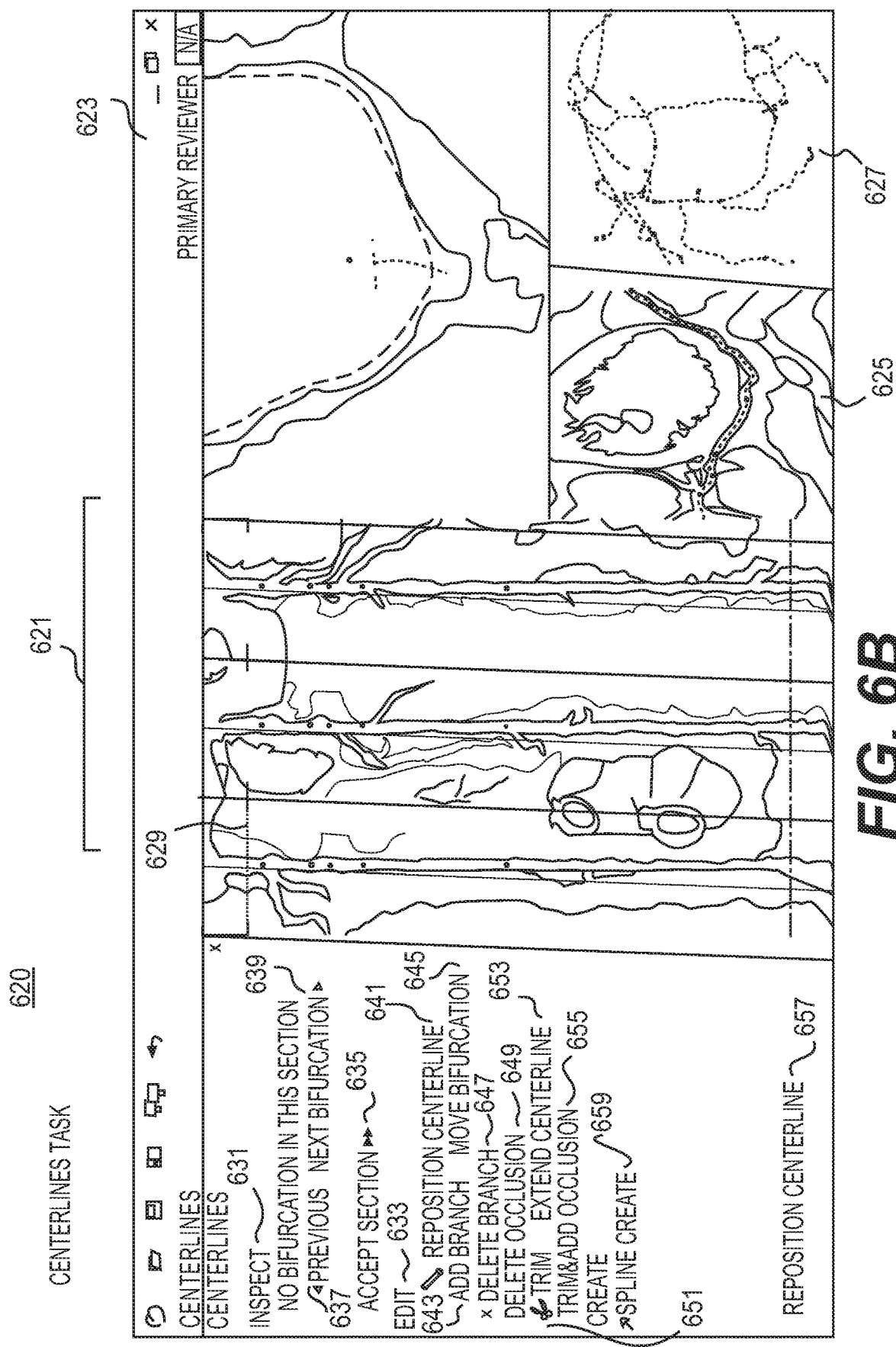
FIG. 6B is a display of centerlines mode, according to an exemplary embodiment of the present disclosure.

FIG. 6B is a display of centerlines mode 620, according to an exemplary embodiment of the present disclosure. In one embodiment, centerlines mode 620 may include six views of angular maximum intensity projections (aMIPs) 621, a view of an MPR 623, a view of a CPR 625, and a view of a VR 627. aMIPs may include views similar in structure to sCPRs in that the display may include image data of an entire length of a centerline in a straightened view. One distinction between an aMIP and a sCPR though, may include the aMIP being based on an MIP taken around a centerline in a wedge shape of 60°, whereas sCPRs are displays based on a plane. In one embodiment, the aMIPs 621 may be arranged on the left side of the display, such that they resemble three sCPR views. The MPR 623 may take up half of the remaining right, vertical space. The CPR 625 and VR 627 may share the remaining space equally. In one embodiment, the aMIPs 621 may display 0°-60°, 180°-240°, 60°-120°, 240°-300°, 120°-180°, and 300°-360° wedges. In one embodiment, the aMIPs 621 may be oriented such that the proximal direction is towards the top of the screen, where the origin of the vessel centerline may be located at the top of the window. In one embodiment, the aMIPs 621 may automatically zoom such that vessels of a certain length fill the screen and vessels longer than the given length are zoomed out such that the entire vessel is visible in the aMIPs 621.

In one embodiment, the MPR 623 may be constrained to rotate about a selected centerline. For example, the MPR 623 may be centered, initially, depending on the currently selected section. If a current section has bifurcation points in the section, an initial center point may be the first bifurcation point in the section. If the section does not have bifurcations, the initial center point may be the center of the section. The MPR 623 may be oriented such that the proximal direction is at the top of the screen, and the MPR 623 may be constructed such that the tangent vector of the center point defines the up and down directions of the view. The initial rotation of the view may also be determined by the section. If the centering point is a bifurcation, initial rotation may be one such that the branch is most visible in the MPR 623. If a bifurcation is not selected, rotation may not update. The MPR 623 may be zoomed such that the section may fill the vertical space of the view. In one embodiment, the MPR 623 may have the same windowing as the aMIPs 621.

In one embodiment, the VR 627 may be cropped to the heart mask. The VR 627 may automatically rotate to display the analyzed section at a center of the screen. In one embodiment, the VR 627 may be oriented such that the superior direction is towards the top of the screen. The VR 627 may be zoomed such that a section is visible in the view.

In one embodiment, navigation in the centerlines mode 620 may be accomplished through interaction with the aMIPs 621 and the MPR 623. Navigation tools for clicking to re-center or probing may be available. In one embodiment, an Inspector Gadget 629 may be an exemplary navigational tool that provides these capabilities. The Inspector Gadget 629 may appear as a colored line when a cursor is detected to be hovering over aMIPs 621 and MPR 623, for instance. The line may be an indication of the probe location. In one embodiment, a user may then click to re-center a view of the MPR 623 to a centerline indicated by Inspector Gadget 629. In one embodiment, the Inspector Gadget 629 may be restricted a selected section and any previously accepted sections on the selected centerline. In such an embodiment, Inspector Gadget 629 may not be operable on unaccepted sections or on sections in different centerlines. In one embodiment, centerlines task 600 may have constrained rotation capabilities. For example, dragging left or right on the aMIPs 621 and/or MPR 623 may enable the constrained rotation. In one embodiment, the rotation may occur at a selected centering point and rotation may be about a tangent to the vessel centerline at the selected centering point. In one embodiment, MPR 623 may be scrolled ten slices above and below the image plane containing the center point.

In one embodiment, tools available in centerlines mode 620 may be separated into different portions of the UI, with each portion sharing the naming scheme of different modes in other tasks. For example, centerlines mode 620 may include an inspect section 631 and edit section 633. The inspect section 631 may include an option that may change a status of a selected section and all bifurcations in the section to "accepted." For example, exemplary tool Accept Section 635 may have such a function of changing the status of the sections and respective bifurcations undergoing analysis. In one embodiment, Accept Section 635 may further operate as a navigational tool, where selection of Accept Section 635 may automatically prompt navigation to the next unaccepted section. Inspect section 631 may further include tools, for example, Previous Bifurcation 637 and Next Bifurcation 639. These tools may also be navigational tools, automatically navigating to the previous or next bifurcation in the section being processed. Selection of Next Bifurcation 639 may also change a status of the currently selected bifurcation to "accepted." Another navigational tool may include an option for navigating to a previous section. In one embodiment, tools may also be bound to keyboard shortcuts, rather than or in addition to appearing as buttons on a display.

Edit section 633 may include several tools, for example, Reposition Centerline 641, Add Branch 643, Move Bifurcation 645, Delete Branch 647, Delete Occlusion 649, Trim 651, Extend Centerline 653, Trim and Add Occlusion 655, Reposition Centerline 657, etc. to edit the centerline position of selected and distal sections. In one embodiment, a user may place control points on MPR 623 to define the location of a centerline. Each newly placed control point may cause a repositioning algorithm to run and update the centerline. In one embodiment, control points may also be moved and deleted. For example, a user may hover a cursor over a control point until it is highlighted in order to move the control point. A user may then click and drag on the highlighted point to move the control point. To delete a control point, a user may hover over the point until it is highlighted. For example, a user may click to select the control point and select Delete Branch 647 or Delete Occlusion 649 to delete a selection. Reposition Centerline 657 may also cause a repositioning algorithm to run when moving or deleting a control point. In one embodiment, Add Branch 643 may add a centerline tree from a location specified on MPR 623 back to a section centerline. A bifurcation added from Add Branch 643 may have a default status of being unaccepted, although it may be presented for processing. Add Branch 643 may connect a centerline from a section being processed, to a placed control point, e.g., creating a straight line path if the algorithm fails to find a likely path.

Move Bifurcation 645 may allow a user to slide a selected bifurcation point up and down a centerline. For example, the bifurcation may only be slid proximally to a next proximal bifurcation and/or slid distally to a next distal bifurcation location. In one embodiment, Move Bifurcation 645 may be operable only when a bifurcation is selected. Thus, if Inspector Gadget 629 is used to move off of a bifurcation point, Previous 637 and Next Bifurcation 639 may be used to select bifurcation points that need to be moved. In one embodiment, use of Move Bifurcation 645 may cause the status of selected sections and any sections through which the bifurcation passes, to change to "unaccepted." Delete Branch 647 may remove the centerline tree and bifurcation point of the selected branch. Like Move Bifurcation 645, Delete Branch 647 may work only if a bifurcation point is selected. Delete Occlusion 649 may remove an occlusion tag for a selected centerline. In one embodiment, Delete Occlusion 649 may be available only if the selected centerline is tagged as an occlusion. Trim 651 may be used to delete a centerline tree distal to a user-specified point. In other words, all pathlines distal to the placed trim point may be removed from the tree. If the trip point is used near a bifurcation point, Trim 651 may cause a bifurcation point to highlight, and Trim 651 may remove the selected pathline, the centerline tree distal to that point, and the bifurcation point. Extend Centerline 653 may create a centerline from a selected centerline terminus to a placed point. In one embodiment, the tool may be available only in the terminus section of the centerline. Trim and Add Occlusion 655 may be used to trim a selected centerline and add an occlusion tag to the centerline. Create Spline 659 may be a tool available in a "create" portion of centerlines task 620. Create Spline 659 may create a spline line from a centerline terminus to user-placed points. In one embodiment, the spline line may continue until a user finalizes the spline by, for example, double-clicking. Create Spline 659 may also only be available in the terminus section of the centerline.

In one embodiment, the intended workflow for centerlines mode 620 may be for a user to review each section in the centerline tree for incorrect centerline placement, incorrect branch identification, incorrect branch placement, missing branch identification, etc. Reposition Centerline 641, Add Branch 643, Move Bifurcation 645, Delete Branch 647, and Delete Occlusion 649 may be used for these reviews. At a terminus section, a user may also check for whether the vessel is extended far enough and whether there should be an occlusion tag on the centerline. Trim 651, Extend Centerline 653, and Trim and Add Occlusion 655 may be used for reviews at the terminus section. In one embodiment, a user may check for correct centerline placement as a first line because the centerline may affect setup of subsequent views. All of the views may be constructed around the vessel centerline, so the placement of the centerline within the vessel may be extremely important.

Next, each branch within the section may be inspected for its correctness. The check may include correct identification, as well as correct placement. If either is incorrect, a user may use Delete Branch 647 and Move Bifurcation 645, respectively, to correct the branch. Finally, centerlines mode 620 may provide capability to inspect for missing branches. For example, a centerline may be added where a branch is seen. If a branch is too small to be reliably included in a model, a suggested trim location may show a location to be near a bifurcation itself. The aMIPs 621 may be used for this activity since branches may be visible in the views in at least one of the aMIPs 621. If anything is seen in the aMIPs 621, a user may place the Inspector Gadget 629 at a location and further inspect the location in the MPR 623.

A special case may exist if a centerline exits the lumen. In this situation, if Reposition Centerline 641 is unable to move the centerline back into the vessel or if the centerline is entering the wrong structures, Trim 651 may be used to cut the centerline. Upon reaching a centerline terminus, a user may decide to extend the centerline or trim the centerline to a more suitable length. A proposed trim location may be provided by centerlines task 620. If a centerline is too short, a user may employ Extend Centerline 653 to add to a centerline length. If a proposed trim location is not yet visible in views, a user may determine that the centerline is still too short. Additionally, if plaque or disease is detected in a vessel, the vessel may be extended. If the vessel is long enough and no plaque is visible, a user may accept a proposed trim location and trim the centerline.

In one embodiment, a user may inspect a centerline tree in a specified order that proceeds vessel to vessel, section by section. The section review may occur from a proximal end to a distal end. For each section, inspection may follow the analysis as described for centerlines task 600. After each section is accepted, a user may reach the terminus section of a selected centerline and check the length of the centerline. After accepting the terminus section, a user may select a next centerline and repeat the process for that centerline.

The centerlines task 600 may include all the modes in one interface (e.g., centerlines mode 620) rather than separating the interface into different modes, like the aorta task 300 and myocardium task 500. Sections may be used to control the extent of the review. For example, tools in centerlines mode 620 may be available for each section (e.g., inspect section 631 and edit section 633) and use may be controlled by each section's properties and process. For example, Create Spline 659 may be operable only when a user is reviewing a centerline terminus section.

In one embodiment, a user may move past centerlines mode 620 when all sections are accepted. Upon acceptance of a last section of the centerline tree, centerlines task 600 may be seen as completed and centerlines labeling task 640 may be activated.

In one embodiment, the centerlines task 600 may include several background calculations not immediately exposed to a user. For example, one set of calculations may include an automatic calculation of sections. For example, sections may be recalculated following any tool that modifies centerline length. In some cases, the recalculation may not affect the workflow. If a user edits a previously accepted section and makes an edit that changes the length of a selected centerline (e.g., an edit, an extension of the centerline, or trimming of the centerline), the section and any distal sections may be updated and their respective status may change to "unaccepted."

In one embodiment, calculations may further include background calculations for the ordering of images and sections for centerline inspection. Centerline inspection may be based on several factors. First, vessels may be ordered by the main vessels (e.g., RCA, LAD, and then LCX) to better support an intuitive guided workflow and standardize ordering. The labels may be available either from user confirmation or automatic pipeline results. If the labels are not available, a first vessel may be selected by length. In one embodiment, the next images may be in order of branches off the main vessels, in order of proximal to distal. The order after that, may be onto branches of branches, in order from proximal to distal. Thus, all second generation branches off a first branch may be reviewed before the second branch and its branches.

Yet another calculation may include a proposed trim location algorithm. The algorithm may place a point on the centerline tree indicating a suggested or proposed trim location, based on a radius estimate of the segmentation. The suggested trim location may be at every centerline leaf vessel, meaning the last segment of centerline from a bifurcation to a vessel terminus point. Therefore, when a centerline is added to a tree, a new suggested trim location may be computed for each newly created leaf vessel.

If a user returns to the centerlines task 600, for example, from lumen task 700, a section selected in lumen mode 720 may be selected automatically in centerlines mode 620 as well. For all other tasks, the last visited section in centerlines mode 620 may be the interface presented to a user when a user returns to centerlines task 600. In most cases, the "last visited section" may be a topology tree. In one embodiment, Accept Section 635 may be unavailable or inaccessible until a tool used on the centerline tree invalidates acceptance of the centerline section.

In one embodiment, a progress bar may overlap a centerlines tab when the centerlines task 600 is active. The bar may track the number of currently viewed sections for the entire tree. As more sections are added, the progress bar may update according to a correct percentage. Similarly, as each section is reviewed and accepted, the bar may automatically fill until all sections are reviewed and accepted.

Figure 6C:
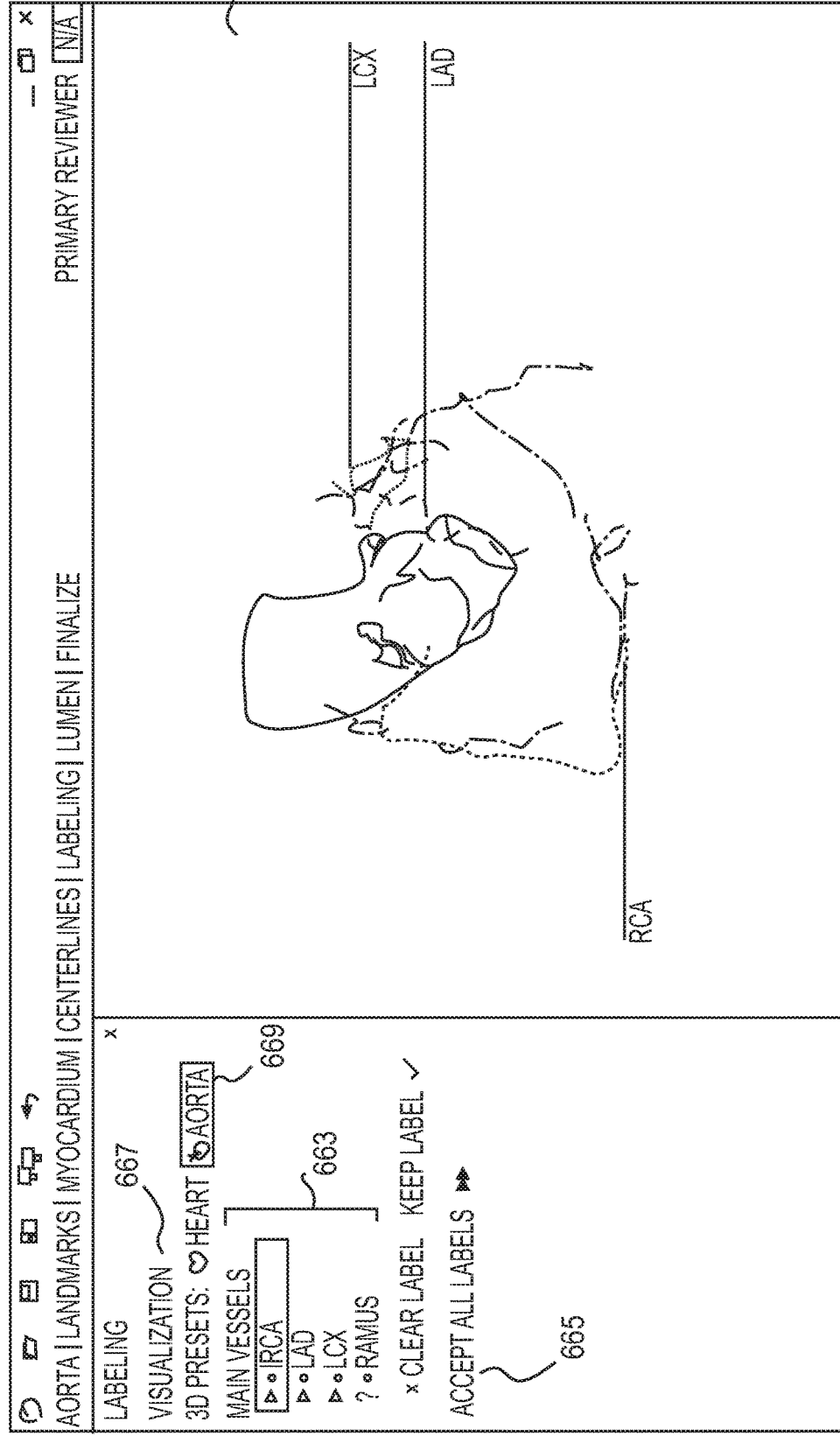
FIG. 6C is a display of centerlines labeling mode, according to an exemplary embodiment of the present disclosure.

FIG. 6C is a display of centerlines labeling mode 640, according to an exemplary embodiment of the present disclosure. In one embodiment, centerlines labeling mode 640 may include providing a user with user interfaces where a user may identify main vessel labels. In one embodiment, labels may be used to determine a correct ordering, perhaps used in the lumen task 700. More importantly, the labels may be used in a final report to report on FFRct values. For example, labels may be identified in the following order: RCA, LAD, LCX, and Ramus. These labels may be used to set vessel-specific dilation factors in pre-solver/solver calculations. In a further embodiment, the labels may inform labeling on a FFRct report. In one embodiment, a user may review all labels and either accept or un-accept the labels in order to proceed to lumen task 700. In other words, such an embodiment may include each vessel having at least one accepted label before activating lumen task 700.

In one embodiment, centerlines labeling mode 640 may include a view that is a VR 661. The VR 661 may have two available masks for use in cropping, e.g., a heart mask and an aorta mask. Each label may have a unique color and/or tag to differentiate and separate between the vessels. In one embodiment, centerlines defined in the centerlines mode 620 may be visible in VR 661.

In one embodiment, centerlines labeling task 640 may include full navigation controls for VR 661. In one embodiment, a label may consistently be selected, so the space bar may be used to enable navigation. The VR 661 may feature synchronization of a centerline point with MPRs in a navigation screen. To synchronize the centerline point between images, a user may double-click on a centerline point on which re-centering may occur.

In one embodiment, centerlines labeling task 640 may include a label list 663. The label list 663 may be used to navigate to a selected label. When a label is selected from the label list 663, a label may highlight and the VR 661 may rotate to the best angle to display the centerline with the selected label displayed.

Tools available in centerlines labeling mode 640 may include tools for label updates and changing label status. To update a centerline label with a new centerline, a user may select a centerline from VR 661. The selected centerline may update with the selected label. To accept a label as correct, a tool, Accept Label 665 may be available. If a label does not exist (e.g., a patient does not have an RCA), an exemplary tool, Clear Label, may be provided. In both cases, the status of a label may change to either an acceptance or clearing the label, respectively, and a next label in the label list 663 may be selected. For example, the LAD label in label list 663 may be selected following a selection of a label for RCA. The process may be repeated for all labels in the label list 663. In one embodiment, the labels themselves may also be selected. This functionality may permit a user to quickly navigate between labels. In the case of either automatic or manual selection, the VR 661 may automatically rotate to display the vessel centerline. If, at any time, a centerline with an existing label is selected, the centerline may update with a currently selected label. The previous label may be cleared and the centerline may have an updated status of "un-reviewed."

The masks for cropping may further aid in identification of labels. In one embodiment, a heart isolation mask 667 may be a default mask for cropping. Where cropping from the heart isolation mask 667 cannot be interpreted, aorta mask 669 may present an alternative cropping mask. If neither mask renders satisfactory results, a user may select a point on which to re-center the navigation screen view of VR 661. In one embodiment, a user may select the point by double-clicking on the vessel centerline. In one embodiment, this option may be a last resort, used if the heart isolation mask 667 and aorta mask 669 are both unable to provide a user with sufficient information to correctly identify vessel labels. In one embodiment, a tool, e.g., Accept All Labels 651 may appear after all vessel labels are either accepted or cleared. Selecting Accept All Labels 651 may activate the next task, lumen task 700. In one embodiment, Accept All Labels 651 may remain unavailable if any labels are not yet reviewed and/or the status of any labels contain any un-reviewed labels.

In one embodiment, no background calculations may be expected to occur for the labeling task itself. However, a centerline order may be redefined from an output of the labeling task of centerlines labeling mode 640. Such a reordering of the centerlines may also result in a reordering and recalculation of sections. These changes may affect lumen task 700.

When returning to the centerlines labeling mode 640 from lumen task 700, labeling and statuses may be the same as when a user left centerlines labeling mode 640. A first label may be selected and Accept All Labels 651 may be inaccessible until a label is changed or a different vessel is selected. If a user returns to the centerline task 600 and makes any edit, a centerline labeling algorithm may be rerun. Then, upon moving to centerlines labeling mode 640, labels may be re-inspected to ensure correct labeling.

In one embodiment, a progress bar may overlap a centerline labeling tab when the centerlines labeling mode 640 is active. Each label's acceptance or clearance may count equally toward a total final, meaning each label may count as 25% of the progress bar. For the centerlines labeling mode 640 display, a label may be selected automatically, as a default. Thus, navigation may be constrained to space bar movement between the labels. In other words, centerlines labeling mode 640 may have an embodiment where a vessel may be absent of a label. In one embodiment, selection of a centerline may be default behavior for a mouse button.

FIG. 7A is a block diagram of an exemplary lumen task 700, according to an exemplary embodiment of the present disclosure. Lumen task 700 may be performed by server systems 106, based on information, images, and data received from physicians 102 and/or third party providers 104 over electronic network 100. In one embodiment, lumen task 700 may be used to segment lumen. In one embodiment, lumen task 700 may generate lumen segmentation for boundary condition definition that may be used for CFD calculations. Like centerlines task 600, a user may start with the RCA, segment the lumen in sections, then proceed with the same steps through review of LAD and LCX trees. In one embodiment, ordering of the vessels may change from ordering in centerlines task 600, for example, due to changes made in centerlines labeling mode 640. In one embodiment, sections may be reviewed from a proximal to distal end of a vessel.

In one embodiment, lumen task 700 may include reviewing each ostium and each centerline of the ostium. Specifically, such a review may occur by reviewing each section. For example, lumen task 700 may start with viewing and assessing each section (step 701). Then, a user may be presented with an option to edit the section (step 703). In one embodiment, a user may determine not to edit the section. Then, a user may elect to accept a section (step 705). Alternately, a user may enter options to edit a segmentation (step 707), after which the lumen task 700 may start again at step 701 for a user to view and assess the section and see whether the section may use editing.

Figure 7B:
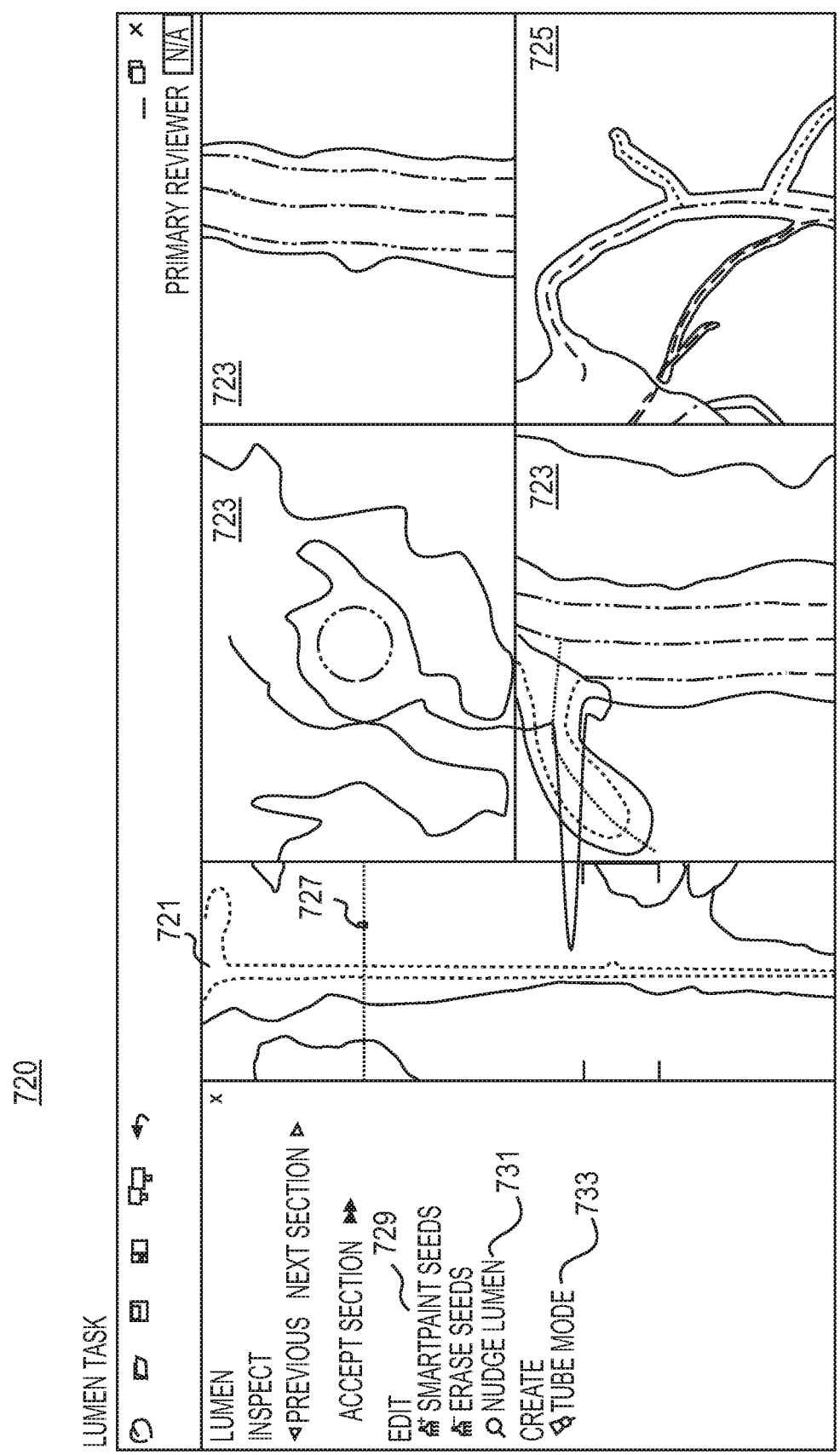
FIG. 7B is a display of lumen mode, according to an exemplary embodiment of the present disclosure.

FIG. 7B is a display of lumen mode 720, according to an exemplary embodiment of the present disclosure. In one embodiment, lumen mode 720 may include an sCPR 721, three MPRs 723, and an ISO 725. In one embodiment, the sCPR 721 may be located on the left of the window, with the MPRs 723 and ISO 725 dividing the remaining space in a 2×2 arrangement. In one embodiment, the ISO 725 may be at the bottom right.

In one embodiment, the sCPR 721 may be oriented such that the proximal direction is at the top of the screen and the distal direction at the bottom. The zoom may be fixed, but may adapt according to a length of the centerline. The one MPR of MPRs 723 may display a longitudinal view of the vessel, where the view may be centered at a current centerline point. The view may be oriented to have a proximal direction of a tangent to the centerline towards the top of the screen. The zoom may also be fixed, but show the entire section. Another MPR of MPRs 723 may show a cross-sectional view or a view of a vessel orthogonal to the centerline. The centering point may be the centerline point, where the zoom may be fixed. Yet another MPR of MPRs 723 may show a lateral view, meaning a view parallel to the z-axis of the dataset. The view may be centered at the centerline point for the views and the view may be oriented such that the anterior direction is towards the top of the screen. The zoom may also be fixed. In one embodiment, the ISO 725 may show the isosurface of a section. The ISO 725 may maintain the same centering, orientation, rotation, and zoom as the top left MPR of MPRs 723.

In one embodiment, a primary navigation tool may include Inspector Gadget 727. In one embodiment, the Inspector Gadget 727 may be active only in a selected section. The MPRs 723 and sCPR 721 may rotate when the Inspector Gadget 727 is rotated and the MPRs 723 may update to the specified centering point when a re-centering operation is performed using the Inspector Gadget 727. In one instance, all three MPRs 723 may act in unison for the rotation and centering. In addition to the Inspector Gadget 727, typical constrained navigation may be available on the MPRs 723. Rotation and centering may be synchronized in all the views.

In one embodiment, lumen task 700 may include Smart Paint 729, Nudge 731, and Tube Mode 733 as exemplary tools. Smart Paint 729 may differ from "Smart Paint" in other tasks. For example, Smart Paint 729 may affect either accepted or unaccepted sections, so Smart Paint 729 may affect segmentation across section boundaries. Preferably, lumen task 700 may mitigate segmentation disconnects that may arise from section boundaries.

In one embodiment, Nudge 731 may also have functionality that is specific to lumen task 700. Because lumen task 700 may include multiple sets of contours, the Nudge 731 may work on contours of parent sections rather than contours of branch sections. This functionality may help Nudge 731 mitigate navigation through previous sections, as well as the various sets of contours. Thus, for a particular section with a bifurcation, Nudge 731 may not affect the contour of a distal branch section when a parent section is selected. When a selected section is a distal branch section, however, Nudge 731 may affect a contour of the parent section. In one embodiment, Tube Mode 733 may permit work between sections. Tube Mode 733 may be a tool used to resolve image artifacts and failures in more semiautomatic algorithms. In one embodiment, lumen task 700 may also feature section-based acceptance of the segmentation. Every section of lumen segmentation may be accepted before finalize task 800 is activated. For example, a subsequent section may be presented for review after a user accepts a section. Once all sections are accepted, finalize task 800 may initiate automatically, in one exemplary workflow.

In one embodiment, lumen task 700 may reorder sections depending on an order from centerlines labeling mode 640. A first section of the RCA centerline may be a default as the section reviewed first. For each section, a user may determine if the segmentation is correct. Smart Paint 729 may be provided for a user to make minor changes. If Nudge 731 is used first, subsequent edits using Smart Paint 729 may override previous edits made by Nudge 731. In one embodiment, lumen task 700 may include different centerline paths with different sets of contours. Separation of the contours may be decided upon to facilitate editing. In one embodiment, edit tools (e.g., Smart Paint 729 and Nudge 731) may help modify different contours of various hierarchies. In this way, a user may help decrease the chances of returning to a previous section to do detailed work, where the work may be facilitated with a view in later portions of the workflow. In one embodiment, Smart Paint 729 may be used for un-reviewed or reviewed sections. In one embodiment, Nudge 731 may work on contours of a proximal or connecting branch. This means in a further embodiment, Nudge 731 may be inoperable for contours of distal sections or of branch vessels. This way, users may use Smart Paint 729 and Nudge 731 to modify bifurcation of both contours, on a branch section. In one embodiment, Smart Paint 729 may modify contours of the parent vessel section and branch section on a parent vessel section, but Nudge 731 may affect only the parent vessel section.

In one embodiment, Tube Mode 733 may be used when a major image artifact affects the way segmentation is calculated using typical tools. Tube Mode 733 may be used across sections, where Tube Mode 733 may employ one diameter across various sections. Smoothing may be performed at the section beginning and end to ensure connectivity in the segmentation. Once a last section is accepted, finalize task 800 may automatically activate and a model may be generated. For the model, individual contours may be integrated to create a single mesh. To move back to a previous task, a user may select a tab associated with the respective task. In one embodiment, various modes of tasks may be unavailable unless a user goes through a particular mode of the task. For lumen task 700, lumen mode 720 may be revisited immediately, especially since the exemplary lumen task 700 includes only one lumen mode 720.

In one embodiment, background calculations may occur after completion of lumen task 700 when a user is moving on to finalize task 800. For example, warnings may be computed when the segmentation is being converted to a model. In one embodiment, a warning may occur if lumen segmentation is separated from aorta segmentation. In another embodiment, a warning may occur if a loop is detected in the segmentation.

In addition to displaying a centering point in the MPRs 723 and Inspector Gadget 727 of the sCPR 721, lumen task 700 may include UI elements. For example, lumen mode 720 may further detect and display misregistrations. To better separate out distinctions between sections, a selected section may have a different contour indicator from other sections' contours. As discussed previously, lumen task 700 may include different sets of contours for the parent vessel and adjoining branch vessels. Thus, various contours may be displayed on the MPRs 723 in different colors.

Figure 8A:
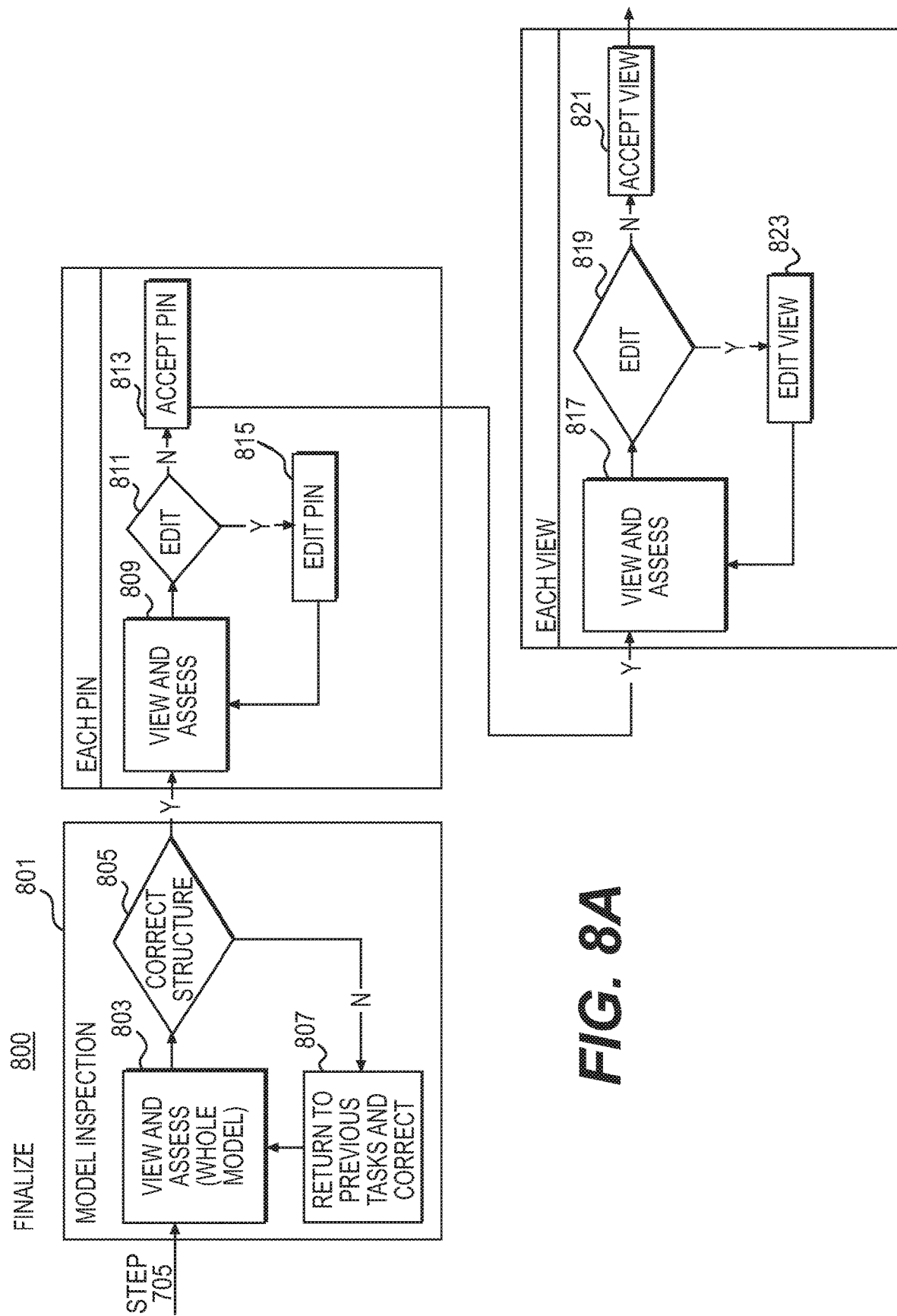
FIG. 8A is a block diagram of an exemplary finalize task, according to an exemplary embodiment of the present disclosure.

FIG. 8A is a block diagram of an exemplary finalize task 800, according to an exemplary embodiment of the present disclosure. Finalize task 800 may be performed by server systems 106, based on information, images, and data received from physicians 102 and/or third party providers 104 over electronic network 100. In one embodiment, finalize task 800 may be used to view the trimmed model, add additional views for a final report, and launch a computational fluid dynamics (CFD) calculation on a server (e.g., on server systems 106). In finalize task 800, a user may view a final model to be used in CFD calculations, cancel or return to a previous task, or proceed with a CFD solution. Finalize task 800 may provide a last verification for a user to approve a model for CFD simulations. In one embodiment, the finalize task 800 may further be used to save views and FFRct locations, for example, for a final report. In some instances, finalize task 800 may serve as a critical step to ensure reports display acceptable views and FFRct locations. In one embodiment, a user may enter the finalize task 800 with a series of steps 801 for inspecting a model. For example, step 803 may include a user viewing and assessing an entire model. The inspection may include looking for holes, and/or missing pieces in segmentation. For instance, the inspection may include step 805 of verifying the model structure as correct or accurate. If a user detects faults in the model or wishes to correct any part of the model, the user may exercise step 807, navigating back to a previous task or user interface mode to make the changes.

If a user approves of the overall model, he may proceed to set up views for the final report. The views may dictate how information from CFD solutions or calculations may be presented and/or accessed. In one embodiment, saved views may serve as a starting point, and the model may be oriented to display each major centerline. In a further embodiment, pins may be placed on the main centerline, distal to any stenoses. The pins may serve as markers for locations on the model, at which FFRct calculations are desired. The pins may further indicate locations of the model where views are desired. Both the FFRct calculations and views may be included in a final report. In one embodiment, a user may proceed to steps 809-815 when he may approve the overall model. In one instance, steps 809-815 may include a process for inspecting each pin. For example, step 809 may include viewing and assessing each pin and step 811 may include editing the pin. Either step 813 or step 815 of accepting the pin or further editing the pin, respectively, may follow the step 811 of editing the pin. In one embodiment, steps 817-823 may include a process for setting up views for a final report. In some cases, the views may include a view displayed for each pin location. Step 817 may include viewing and assessing each view, step 819 may include editing the view, and then steps 821 and 823, respectively, may include either accepting the view or editing the view.

When all changes are complete, finalize task 800 may launch the CFD solution and close the workstation.

Figure 8B:
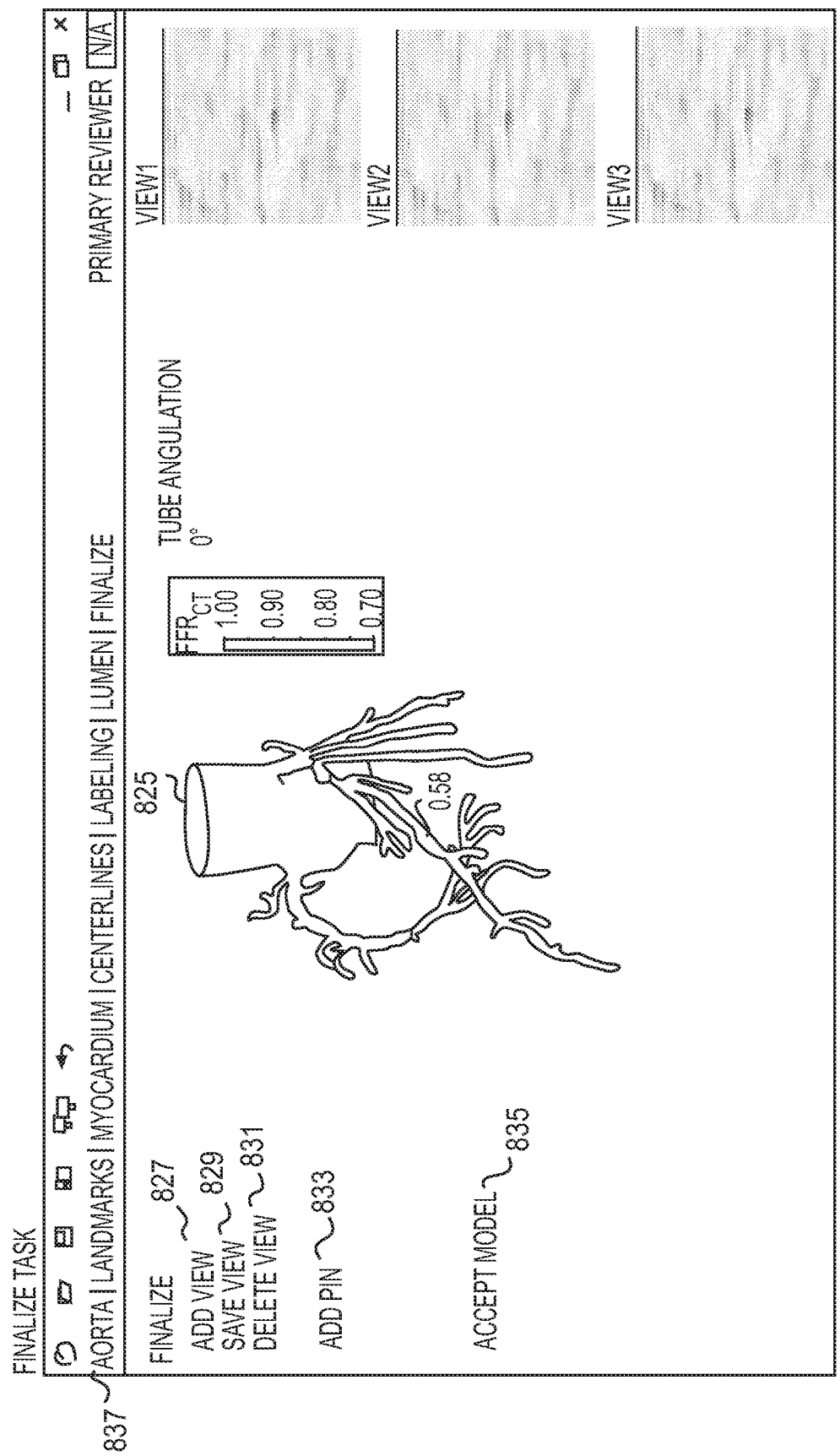
FIG. 8B is a display of finalize mode 820, according to an exemplary embodiment of the present disclosure.

FIG. 8B is a display of finalize mode 820, according to an exemplary embodiment of the present disclosure. In one embodiment, finalize mode 820 may depict an exemplary interface by which a user may view the final model used in CFD calculations. Furthermore, finalize mode 820 may provide a user with a last step to either cancel and return to a previous task, or to proceed with the CFD solution. In one embodiment, the finalize mode 820 may feature a trimmed mesh model 825 of the lumen and aorta segmentation generated from previous tasks. In one embodiment, the model 825 may be rotated in any of the axes so views may be adequately set up for a final report. Panning the model may also be an option provided in the finalize mode 820. In some embodiments, finalize mode 820 may not include some navigational tools, e.g., tools for re-centering.

In one embodiment, the finalize mode 820 may feature tools for generating and saving views for a final report, including ways to save an existing orientation as a view, recall saved views, delete saved views, and overwrite saved views. These tools may include, for instance, Add View 827, Save View 829, and Delete View 831. The finalize mode 820 may further include tools for placing FFRct pins (e.g., a tool, Add Pin 833). In one embodiment, the finalize task 800 may serve as a last task for a workstation, meaning a final check before the model exits an analyst's workspace. If the model is verified and approved as complete, no final edits are to be made, and all views are set up, a user may launch a CFD solution from the finalize mode 820. For example, a user may use Accept Model 835 to close the workstation and launch the CFD solution. If a user wishes to return to a previous task, a task bar 837 may be used to navigate to a previous task.

Moving from the lumen task 700 to the finalize task 800 may include numerous background calculations. In one embodiment, one background calculation may include a union of the multiple disjoint segmentations to create a single segmentation. A further background calculation may include trimming the segmentation and/or defining boundary condition planes, for example, an aorta inlet, aorta outlet, and all vessel outlets. The aorta inlet and outlet may be defined according to centerlines from lumen task 700. Outlets may be circularized, at least to some degree, including the aorta inlet plane. In some embodiments the aorta inlet plane may be more circularized than other outlets. In addition to trimming, other background calculations may include calculating views based on 'standard' RAO/LAO orientations. The views may be calculated automatically and/or adjusted by a user. Whether views are automatic or user-created, tube angulation may be calculated and saved. Furthermore, a background calculation may include calculating FFRmI. In some embodiments, model 825 of finalize mode 820 may display the calculated FFRmI.

In one embodiment, the finalize mode 820 may include several user interface elements to help a user set up and review a final model. For example, pre-canned views with 'standard' CT tube orientations may be available for display. If a model is rotated and saved, a tube orientation at that time may be automatically saved to the view. Furthermore, centerline labels may be displayed, to serve as a last opportunity for a user to check the labels for accuracy or appropriateness, and to ensure that each main vessel is marked with an FFRct pin. Another user interface element may include a progress bar. Acceptance of each saved or prepared view may count as an equal portion of the progress bar, such that as more views are added, the proportion of each view may adjust with a new total. The progress bar for the finalize task 800 may be visible only in the finalize mode 820.

Figure 9:
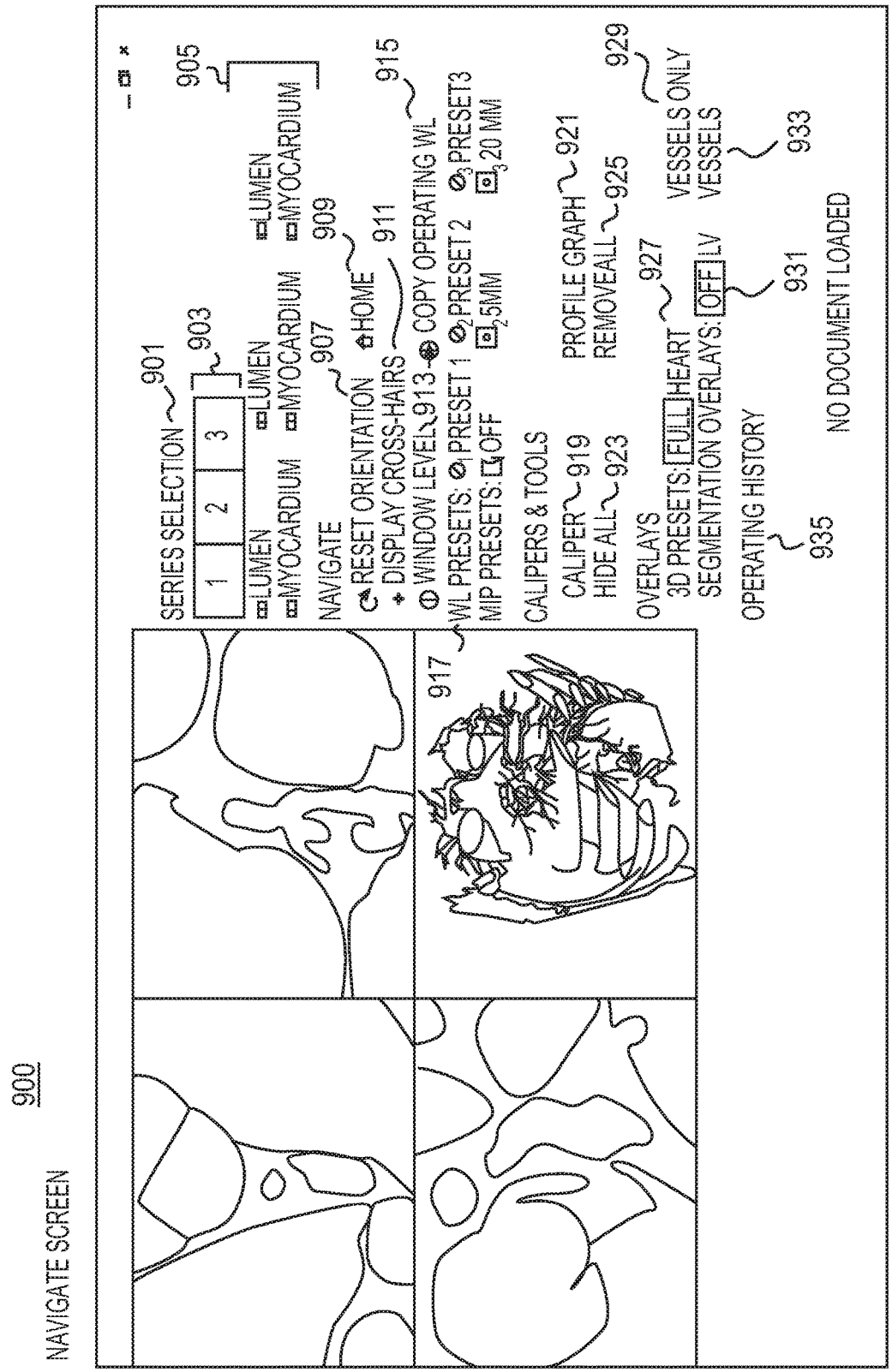
FIG. 9 is a display of navigate mode 900, according to an exemplary embodiment of the present disclosure.

FIG. 9 is a display of navigate mode 900, according to an exemplary embodiment of the present disclosure. Using the navigate mode 900, a user may interact with a secondary viewer screen, separate from the actual processing of the lumen and myocardium segmentations. In situations where the locked down views of the operating visualizations do not provide enough information, and full navigation, windowing, or an alternate series is needed, the navigate mode 900 may be available to provide more information for the user. In one embodiment, the navigate mode 900 may permit a user to navigate feely and provide as much information to a user as possible. At the same time, the workstation is intended to provide a guided workflow. Since the navigate mode 900 may counteract the intent of providing guidance through a guided workflow, the navigate mode 900 may be initially hidden. However, in situations where provided views following a guided workflow may not provide enough information to make an accurate segmentation, for example, the navigate mode 900 may be available to help a user view the data.

Since the navigate mode 900 is meant to provide additional information to a user, tools that affect segmentation may not be provided in the navigate mode 900. Rather, views and tools may be provided to navigate, measure, and display dates, for instance, of data processed in other modes. Additionally, since information may be obtained from various series, a user may select additional series to display side-by-side with views to any operate screen MPRs (e.g., MPRs dependent on the sCPR, although if no operate screen MPRs are available, there may be no effect on zoom). In the exemplary navigate mode 900, up to two other additional series may be selected for display (e.g., series 903).

In one embodiment, a Copy Operating View tool may be provided on a three-dimensional view in an operating screen. This tool may change the re-centering point in MPR views in the navigate mode 900 to the selected re-centering point in the operating screen, reorient MPR views in the navigate screen to display coronal, sagittal, and transverse planes, and have no effect on an existing zoom level in the navigate mode 900. The Copy Operating View tool on an aMIP view in an operating screen may change the re-centering point of MPR views in the navigate mode 900 to a re-centering point along the centerline, orient the navigate mode 900 MPR views orthogonal to an aMIP centerline, and possibly change the zoom level of the navigate mode 900 MPR views to any operating screen MPRs dependent on the aMIP.

In one embodiment, the navigate mode 900 may include three MPRs and a VR view arranged in a 2×2 layout. The MPRs may initially show transverse, coronal, and sagittal planes. In addition, the MPRs may be centered based on the image volume center. As an initial view, the MPRs may be initially zoomed such that the image volume fills at least one of the views. The MPRs may have the same window/level, set to an automatic preset. The three MPRs may share a centering point, zoom, and window/level. Rotation may be synchronized between the three MPRs such that the planes being displayed at any time may be kept orthogonal.

In one embodiment, the VR view may display an entire dataset, but cropping presets may exist to display the data cropped with a particular segmentation. The VR may be orientated such that the superior direction may be kept towards the top of the screen. The VR may be centered such that center of the data is at the center of the view, and the VR may be zoomed such that an entire dataset is displayed.

In one embodiment, full navigation may be available on all views, where the MPRs and the VR may include options for re-centering, zooming, panning, rotation, and windowing. The user may also reset the orientation so the MPR views reorient to the transverse, coronal, and sagittal planes while the centering point, zoom, and windowing may remain the same. The user may also activate a home navigation functionality, where the home command may reset an orientation so the MPR views reorient to the transverse, coronal, and sagittal planes, reset the centering point to the center of the dataset, reset the zoom to encompass the entire dataset, and maintain the windowing.

In one embodiment, the navigate mode 900 may also provide a user with options to synchronize the screen views to some degree, with the information that is displayed in an operating screen. By double-clicking on any view in an operating screen, a corresponding image may be displayed in the navigate mode 900. This functionality may be part of the functionality of Copy Operating View. For example, if a user double-clicks in an MPR view in an operating screen, one MPR in the navigate mode 900 may change the zoom, re-centering point, and orientation to replicate those currently displayed in the operating screen. Copy Operating View on a CPR or sCPR view in the operating screen may change the re-centering point of the MPR views in the navigate mode 900 to the re-centering point along the centerline, orient the navigate mode 900 MPR views orthogonal to the sCPR centerline, and change the zoom level of the navigate mode 900 MPR views to any operating screen MPRs dependent on the sCPR.

In one embodiment, tools available in the navigate mode 900 may be separated into several sections, e.g., a series selection section, a navigate section, a section of measuring tools, and a section of overlay options. For series selection tools 901, up to three series 903 may be available for selection. When a series is selected, data displayed in the navigate mode 900 may be updated to the selected series. Other view properties (like centering point, windowing, zoom level, etc.) may not be affected by a change in series. In one embodiment, a user may also view and select the series for lumen and myocardium processing from checkboxes 905 below the series display.

The navigate section may contain several tools for navigating through the data. For instance, a tool, Reset Orientation 907, may reorient MPR views when activated. For example, Reset Orientation 907 may prompt the MPR views to display coronal sagittal, and transverse plans while preserving existing zoom, window width, and window level. When activated, Home 909 may orient MPR views to display coronal, sagittal, and transverse planes, reset the zoom to encompass the entire image volume, and preserve an existing window width and window level. When activated, a too, Crosshairs 911 may display several crosshairs on MPR views. The crosshairs may be colored and/or automatically update when navigation is performed on the MPRs. In some cases, the crosshairs may continually be synchronized. When activated, Window Level 913 may adjust window width and window level as a user drags a cursor from left to right and top to bottom, respectively. When activated, a Copy Operating WL 915 may adjust window width and window level of the MPR views in the navigate mode 900 to the same window width and window level settings existing at the moment in the operate screen. In the WL Preset 917, a selection of a preset may adjust windowing of all MPRs in the navigate mode 900 to a particular window/level preset. Selection of a preset may turn MIP on or off, with a displayed thickness.

In one embodiment, another section may contain various measuring tools. For example, a Caliper 919 may permit a user to place a measuring line in MPR views of a navigate mode 900. When activated, a too, Profile Graph 921, may allow a user to place a graph displaying Hounsfield units along a line in MPR views in the navigate mode 900. Calipers and profile graphs may be toggled to switch between the two measuring tools. When activated, Hide All 923 may hide all measurements for a currently selected image volume. When activated, Remove All 925 may delete measurements for a currently selected image.

Yet another section may include several overlay options for screen views in the navigate mode 900. For a 3D view, available options may include "full," "heart," and "vessels only." When activated, Full 927 may display a volume rendering for a selected image volume cropped by a heart isolation mask. When activated, Vessels Only 929 may display a volume rendering for a selected image volume cropped by the coronary segmentation. For the MPR views, available options may include "off, "LV," and "vessels." When activated, Off 931 may display work done in the myocardium task 500. When activated, Vessels 933 may display work done in the aorta task 300, centerlines task 600, and/or the lumen task 700. The final section in the navigate mode 900 may include actions performed for the entire case. The list may be used to undo and redo previous work (e.g., actions performed in the operating screens). In some cases, the list may be activated by a too, Operating History 935. In one embodiment, the list may be populated and shared for the entire case, so even series switches and actions performed on other series may be saved.

In one embodiment, background calculations for the navigate mode 900 may include calculations performed for the measurement tools. For example, Caliper 919 may lay down a 2D length measurement tool and display the length of the laid-down line in millimeters. Profile Graph 921 may display the Hounsfield units of the voxels underneath the laid-down line.

In one embodiment, the navigate mode 900 may include several user interface (UI) elements unique to the navigate mode 900. First, for a series display, the currently displayed dataset in the navigate mode 900 may be indicated by a highlighted selection. In some cases, a series displayed in the navigate mode 900 may be different from a series displayed in an operating screen. The series displayed in the operating screen may be selected for lumen processing or for myocardium processing, depending on the currently activated task in the operating screen. The selected case or series may be indicated by the set of checkboxes underneath the series selection set of tools. Additionally, the confidence of each algorithm may be output and displayed next to the selection indicators.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of manipulating medical image annotations, the method comprising:
   receiving an image of at least a portion of an individual's anatomy;
   producing a set of annotations for annotating anatomical features automatically identified by a processor within the image of at least the portion of the individual's anatomy;
   determining a sequence of dependencies between at least two annotations of the set of annotations based on the anatomical features associated with each of the at least two annotations of the set of annotations, the sequence of dependencies being preconfigured prior to receiving the image, the anatomical features including one or more of an aorta, a vessel centerline, and a vessel lumen, wherein the sequence of dependencies defines an order according to which a first annotation of the at least two annotations is followed by a second annotation of the at least two annotations, and wherein the second annotation is dependent upon the first annotation such that an identification of the second annotation is based on a prior identification of, or modification to, the first annotation;
   presenting the set of annotations to a user for validation, the presenting including presenting the first annotation and the second annotations in the order;
   upon validation, by the user, of the set of annotations including the first annotation and the second annotation, determining one or more critical parameters associated with the set of annotations, the one or more critical parameters including one or more of: a size of the annotation, a shape of the annotation, an appearance of the annotation, a density of the annotation, or a relationship of the annotation to other annotations among the set of annotations;
   identifying a critical subset of the set of annotations based on values of the one or more critical parameters; and
   presenting the critical subset of the set of annotations to the user or to another user.

2. The method of claim 1, wherein
   the presenting the set of annotations includes presenting a selected annotation of the set of annotations earlier if another annotation of the set of annotations is dependent on the selected annotation of the set of annotations.

3. The method of claim 2, further comprising:
   requesting validation for the selected annotation of the set of annotations prior to presenting the another annotation of the set of annotations.

4. The method of claim 1, further comprising:
   requesting validations for the critical subset of the set of the image annotations.

5. The method of claim 1, further comprising:
   receiving one or more modifications to the set of annotations based on tools associated with one or more visualizations of the set of annotations.

6. The method of claim 5, further comprising:
   determining one or more dependent annotations in the set of annotations, wherein the one or more dependent annotations are associated with the one or more modifications; and
   determining a re-computation of the one or more dependent annotations in the set of annotations based on the one or more modifications.

7. A system for manipulating medical image annotations, the system comprising:
   a data storage device storing instructions for manipulating medical image annotations; and
   a processor configured to execute the instructions to perform a method including:
   receiving an image of at least a portion of an individual's anatomy;

producing a set of annotations for annotating anatomical features automatically identified by a processor within the image of at least the portion of the individual's anatomy;

determining a sequence of dependencies between at least two annotations of the set of annotations based on the anatomical features associated with each of the at least two annotations of the set of annotations, the sequence of dependencies being preconfigured prior to receiving the image, the anatomical features including one or more of an aorta, a vessel centerline, and a vessel lumen, wherein the sequence of dependencies defines an order according to which a first annotation of the at least two annotations is followed by a second annotation of the at least two annotations, and wherein the second annotation is dependent upon the first annotation such that an identification of the second annotation is based on a prior identification of, or modification to, the first annotation;

presenting the set of annotations to a user for validation, the presenting including presenting the first annotation and the second annotations in the order;

upon validation, by the user, of the set of annotations including the first annotation and the second annotation, determining one or more critical parameters associated with the set of annotations, the one or more critical parameters including one or more of: a size of the annotation, a shape of the annotation, an appearance of the annotation, a density of the annotation, or a relationship of the annotation to other annotations among the set of annotations;

identifying a critical subset of the set of annotations based on values of the one or more critical parameters; and presenting the critical subset of the set of annotations to the user or to another user.

8. The system of claim 7, wherein
the presenting the set of annotations includes presenting a selected annotation of the set of annotations earlier if another annotation of the set of annotations is dependent on the selected annotation of the set of annotations.

9. The system of claim 8, wherein the system is further configured for:
requesting validation for the selected annotation of the set of annotations prior to presenting the another annotation of the set of annotations.

10. The system of claim 7, wherein the system is further configured for:
requesting validations for the critical subset of the set of the image annotations.

11. The system of claim 7, wherein the system is further configured for:
receiving one or more modifications to the set of annotations based on tools associated with one or more visualizations of the set of annotations.

12. The system of claim 11, wherein the system is further configured for:
determining one or more dependent annotations in the set of annotations, wherein the one or more dependent annotations are associated with the one or more modifications; and determining a re-computation of the one or more dependent annotations in the set of annotations based on the one or more modifications.

13. A non-transitory computer readable storage medium for use on a computer system containing computer-executable programming instructions for performing a method of manipulating medical image annotations, the method comprising:

receiving an image of at least a portion of an individual's anatomy;

producing a set of annotations for annotating anatomical features automatically identified by a processor within the image of at least the portion of the individual's anatomy;

determining a sequence of dependencies between at least two annotations of the set of annotations based on the anatomical features associated with each of the at least two annotations of the set of annotations, the sequence of dependencies being preconfigured prior to receiving the image, the anatomical features including one or more of an aorta, a vessel centerline, and a vessel lumen, wherein the sequence of dependencies defines an order according to which a first annotation of the at least two annotations is followed by a second annotation of the at least two annotations, and wherein the second annotation is dependent upon the first annotation such that an identification of the second annotation is based on a prior identification of, or modification to, the first annotation;

presenting the set of annotations to a user for validation, the presenting including presenting the first annotation and the second annotations in the order;

upon validation, by the user, of the set of annotations including the first annotation and the second annotation, determining one or more critical parameters associated with the set of annotations, the one or more critical parameters including one or more of: a size of the annotation, a shape of the annotation, an appearance of the annotation, a density of the annotation, or a relationship of the annotation to other annotations among the set of annotations;

identifying a critical subset of the set of annotations based on values of the one or more critical parameters; and presenting the critical subset of the set of annotations to the user or to another user.

14. The non-transitory computer readable storage medium of claim 13, wherein
the presenting the set of annotations includes presenting a selected annotation of the set of annotations earlier if another annotation of the set of annotations is dependent on the selected annotation of the set of annotations.

15. The non-transitory computer readable storage medium of claim 14, the method further comprising:
requesting validation for the selected annotation of the set of annotations prior to presenting the another annotation of the set of annotations.

* * * * *